US012770739B2

(12) United States Patent
Chahine et al.

(10) Patent No.: US 12,770,739 B2
(45) Date of Patent: Oct. 20, 2026

(54) SERUM CYTOKINE PROFILE PREDICTIVE OF RESPONSE TO NON-SURGICAL LOW BACK PAIN TREATMENT

(71) Applicant: The Trustees of Columbia University in the City of New York, New York, NY (US)

(72) Inventors: Nadeen Chahine, New York, NY (US); Hayley Jacobsen, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1382 days.

(21) Appl. No.: 17/123,373

(22) Filed: Dec. 16, 2020

(65) Prior Publication Data

US 2021/0104329 A1 Apr. 8, 2021

Related U.S. Application Data

(63) Continuation of application No. PCT/US2019/038672, filed on Jun. 24, 2019.

(60) Provisional application No. 62/688,501, filed on Jun. 22, 2018.

(51) Int. Cl.

| | |
|---|---|
| ***G16H 50/30*** | (2018.01) |
| ***G16B 25/10*** | (2019.01) |
| ***G16H 10/40*** | (2018.01) |
| ***G16H 20/17*** | (2018.01) |
| ***G16H 50/20*** | (2018.01) |

(52) U.S. Cl.

CPC ............. *G16H 50/30* (2018.01); *G16B 25/10* (2019.02); *G16H 10/40* (2018.01); *G16H 20/17* (2018.01); *G16H 50/20* (2018.01)

(58) Field of Classification Search

None

See application file for complete search history.

(56) References Cited

U.S. PATENT DOCUMENTS

| | | | |
|---|---|---|---|
| 5,646,005 | A | 7/1997 | Kudsk |
| 9,551,713 | B2 | 1/2017 | Kamat et al. |
| 2005/0244874 | A1 | 11/2005 | Kastelein et al. |
| 2005/0287593 | A1 | 12/2005 | Kastelein et al. |
| 2008/0280862 | A1* | 11/2008 | Cermak .................. A61P 19/04 514/171 |
| 2010/0098684 | A1 | 4/2010 | Scuderi et al. |
| 2011/0014205 | A1* | 1/2011 | Schaeffer ............. A61K 31/537 514/415 |
| 2011/0045476 | A1 | 2/2011 | Barken et al. |
| 2011/0251099 | A1 | 10/2011 | Visvanathan et al. |
| 2014/0081659 | A1 | 3/2014 | Nawana et al. |
| 2016/0063205 | A1* | 3/2016 | Moturu ................. G16H 40/67 705/3 |

OTHER PUBLICATIONS

Risbud, M. et al. Role of Cytokines in Intervertebral Disc Degeneration: Pain and Disc-content. Nat Rev Rheumatol. Oct. 29, 2013;10 (1):44-56. (Year: 2013).*

Bentzer et al. "Plasma cytokine levels predict response to corticosteroids in septic shock", Intensive Care Med vol. 42 / Issue 12, pp. 1970-1979, 2016 [10 pages].

Clinical Trial NCT01007058, "Markers of Response to Intravesical Bladder Cancer Therapy", sponsor: M.D. Anderson Cancer Center, first posted Nov. 3, 2009 [10 pages].

Kamat et al. "Cytokine Panel for Response to Intravesical Therapy (CyPRIT): Nomogram of Changes in Urinary Cytokine Levels Predicts Patient Response to Bacillus Calmette-Guérin", Eur. Urol., vol. 69 / Issue 2, pp. 197-200, 2016 [7 pages].

Weber et al. "Developments in intervertebral disc disease research: pathophysiology, mechanobiology, and therapeutics", Curr Rev Musculoskelet Med. 2015; 8(1): pp. 18-31 [14 pages].

Weber KT et al., "Serum levels of the proinflammatory cytokine interleukin-6 vary based on diagnoses in individuals with lumbar intervertebral disc diseases", Arthritis Res Ther., vol. 18 / Issue 3, Doi: 10.1186/s13075-01500887-8, Jan. 2016.

Weber KT et al., "Exploratory study for identifying system biomarkers that correlate with pain response in patients with intervertebral disc disorders", Immunol Res. vol. 63 / Issues 1-3, pp. 170-180, Dec. 2015.

Chen T et al., "Cytokine and Antibody Based Diagnostic Algorithms for Sputum Culture-Positive Pulmonary Tuberculosis", PLoS One, vol. 10 / Issue 12, E0144705 Jun. 24, 2015.

Chahine, Nadeen O., "Mechanobiology of Inflammation in the Intervertebral Disc", NIH Grant #: 7R01AR069668-02, Sep. 21, 2017.

Kwon BK et al., "Cerebrospinal fluid inflammatory cytokines and biomarkers of injury severity in acute human spinal cord injury", J Neurotrauma, vol. 27 / Issue 4 pp. 669-682, Apr. 2010.

* cited by examiner

*Primary Examiner* — Clinton A Brooks
*Assistant Examiner* — Nicola Maria Bauer
(74) *Attorney, Agent, or Firm* — LEASON ELLIS LLP

(57) ABSTRACT

A method for treating a patient suffering from a pain condition is provided by obtaining a plurality of biometric measurement values for the patient, wherein the plurality of biometric measurement values includes at least (i) a plurality of cytokines measurement levels, and (ii) at least one clinical data value; providing, using a computer configured by code executing therein, the plurality of biometric measurement values as inputs to a predictive model. The predictive model is configured to output a pain responsive likelihood value in response to the input values. The method also includes the step of comparing, using the computer, the pain responsive likelihood value to a pre-determined threshold value, and categorizing, using the computer, the patient as treatment positive where the pain responsive likelihood value is equal to or greater than the threshold value.

10 Claims, 7 Drawing Sheets

FIG. 7

Regression Summary for Dependent Variable: VAS % Difference (ESI DrawA scaled)
R= .97227026 $R^2$= .94530946 Adjusted $R^2$= .87238874
F(20,15)=12.964 p<.00000 Std.Error of estimate: 12.916

| N=36 | b* | Std.Err. of b* | b | Std.Err. of b | t(15) | p-value |
|---|---|---|---|---|---|---|
| Intercept | | | -114.056 | 27.10138 | -4.20856 | 0.000760 |
| LIF Draw A | 0.46908 | 0.103530 | 21.134 | 4.66451 | 4.53083 | 0.000398 |
| CTACK Draw A | 0.29219 | 0.076714 | 24.660 | 6.47453 | 3.80877 | 0.001712 |
| IL-17 Draw A | -1.12450 | 0.224493 | -56.598 | 11.29912 | -5.00905 | 0.000156 |
| IL-13 Draw A | 0.10689 | 0.120376 | 4.829 | 5.43857 | 0.88795 | 0.388582 |
| BMI | 0.47316 | 0.096364 | 67.444 | 13.73586 | 4.91007 | 0.000189 |
| MIP-1a Draw A | 0.72124 | 0.170934 | 53.081 | 12.58036 | 4.21938 | 0.000743 |
| MIP-1b Draw A | -0.75977 | 0.109854 | -88.224 | 12.75619 | -6.91617 | 0.000005 |
| HGF Draw A | 0.79385 | 0.183375 | 67.477 | 15.58674 | 4.32913 | 0.000596 |
| IL-5 Draw A | 0.66198 | 0.127609 | 34.282 | 6.60858 | 5.18752 | 0.000110 |
| GROa Draw A | -0.58945 | 0.112963 | -24.817 | 4.75606 | -5.21807 | 0.000104 |
| IL-8 Draw A | 0.64478 | 0.156057 | 60.439 | 14.62816 | 4.13169 | 0.000887 |
| M-CSF Draw A | -0.33538 | 0.158478 | -26.426 | 12.48731 | -2.11626 | 0.051455 |
| CRP Draw A | 0.07265 | 0.109042 | 2.649 | 3.97572 | 0.66623 | 0.515381 |
| IL-2Ra Draw A | 0.10068 | 0.626523 | 5.280 | 32.85998 | 0.16069 | 0.874481 |
| IL-3 Draw A | 3.17437 | 1.783374 | 42.005 | 23.59866 | 1.77998 | 0.095341 |
| IL-1ra Draw A | -7.87364 | 2.451806 | -101.923 | 31.73837 | -3.21136 | 0.005827 |
| IP-10 Draw A | -0.23283 | 0.115542 | -23.100 | 11.46319 | -2.01514 | 0.062175 |
| MMP-9 Draw A | 0.24737 | 0.107218 | 20.229 | 8.76771 | 2.30719 | 0.035724 |
| IL-1b Draw A | 4.29601 | 2.596995 | 63.429 | 38.34402 | 1.65422 | 0.118851 |
| IL-4 Draw A | -0.16073 | 0.139168 | -35.094 | 30.38599 | -1.15494 | 0.266181 |

SERUM CYTOKINE PROFILE PREDICTIVE OF RESPONSE TO NON-SURGICAL LOW BACK PAIN TREATMENT

CROSS REFERENCE TO OTHER APPLICATIONS

The present application is a continuation of PCT Application No. PCT/US2019/038672, filed on Jun. 24, 2019, which claims priority to U.S. Patent Application Ser. No. 62/688,501, filed on Jun. 22, 2018, each of which are incorporated by reference as if expressly set forth in its entirety herein.

FIELD OF THE INVENTION

The present invention relates to improved systems, methods, processes and kits for evaluating treatment options for patients with low back pain. In particular, the present invention relates to methods for determining an appropriate or effective non-surgical treatment for patients with low back pain.

BACKGROUND OF THE INVENTION

Low back pain (LBP) is the leading cause of disability worldwide. Two common causes of LBP are herniated discs (HD) and intervertebral disc degeneration (IVD). Intervertebral disc (IVD) degeneration is a leading cause of disability. These afflictions result in decreased economic activity, and result in a significant economic burden of about $100 billion per year. Treatments for LBP can be non-surgical (i.e., analgesics, muscle relaxants, epidural steroid injections (ESI)) or surgical (i.e., decompressing impinged nerves, removing the inflammatory material (discectomy)). Treatment of LBP remains controversial, in part, because patient responsiveness varies widely and because there are no reliable methods to predict response to treatment.

Thus, there is a need for new approaches to improve the treatments of LBP and to reverse the associated morbidity and mortality. What is needed in the art are methods, systems and approaches that permit a care provider and/or patient to understand which treatments will have the greatest chance of success in alleviating the pain of the patient.

SUMMARY OF THE INVENTION

In one or more implementations, systems and methods for treatment of a patient suffering from a pain condition are provided. By way of non-limiting example, a method for treating a patient suffering from a pain condition is provided where the method comprises obtaining a plurality of biometric measurement values for the patient, wherein the plurality of biometric measurement values includes at least (i) a plurality of cytokines measurement levels, and (ii) at least one clinical data value and providing, using a computer configured by code executing therein, the plurality of biometric measurement values as inputs to a predictive model. In one particular configuration, the predictive model is configured to output a pain responsive likelihood value in response to the input values, wherein the predicative model is derived using a stepwise multiple linear regression analysis of a dataset of treatment outcomes. The method also includes the step of comparing, using the computer, the pain responsive likelihood value to a pre-determined threshold value, and categorizing, using the computer, the patient as treatment positive where the pain responsive likelihood value is equal to or greater than the threshold value. In a further configuration, the method also includes administering to a patient classified as pain treatment responsive, a pain treatment, such as an epidural steroid injection.

In an alternative arrangement, a system for treating a patient suffering from a pain condition is provided. In one implementation, the system includes one or more multiplex assays configured to determine circulating cytokine levels of a patient. The system also includes a processor, configured by code executing therein, to obtain a plurality of biometric measurement values for the patient, wherein the plurality of biometric measurement values includes at least (i) a plurality of cytokines measurement levels, and (ii) at least one clinical data value. The processor of the system described is configured by code executing therein, to provide the plurality of biometric measurement values as inputs to a predictive model. In one particular configuration, the predictive model is configured to output a pain responsive likelihood value in response to the input values. The processor of the system is also configured to compare the pain responsive likelihood value to a pre-determined threshold value and categorize the patient as treatment positive where the pain responsive likelihood value is equal to or greater than the threshold value.

BRIEF DESCRIPTION OF THE DRAWINGS

The present invention may be best understood by reference to the following detailed description taken in conjunction with the accompany drawings, wherein:

FIG. 7 is a table detailing the regression summary for the predictive model described herein.

DETAILED DESCRIPTION OF EXEMPLARY EMBODIMENTS

Figure 1:
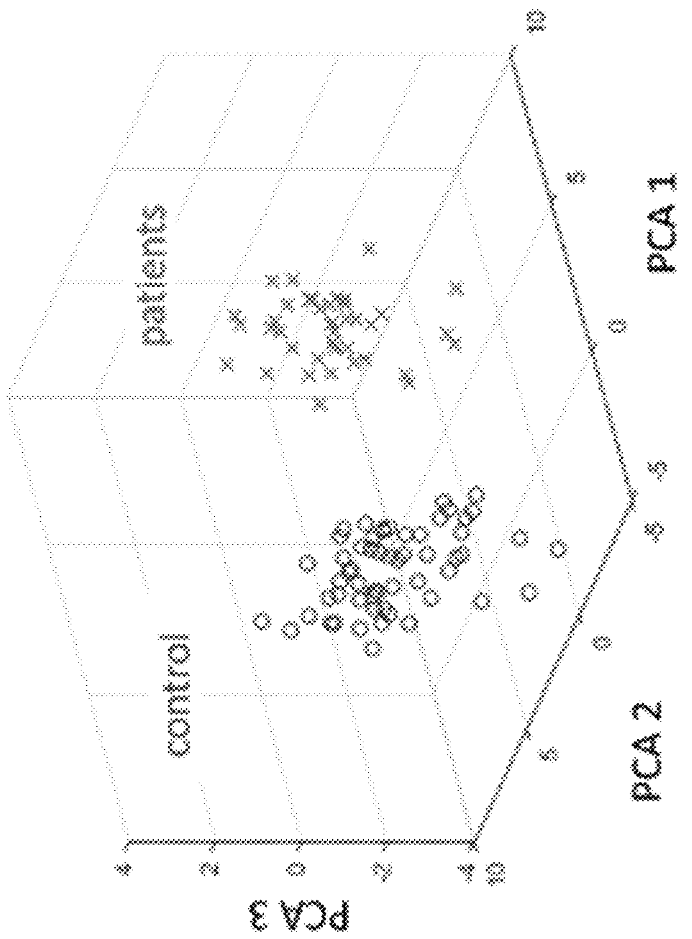
FIG. 1 is a plot of PCA of serum cytokine profiles measured in control subjects vs. disc disease patients.

As used herein, the terms “radicular pain”, “radiculopathy”, radiculopathic pain” and “sciatica” refer to radiating pain of the extremities which emanates from the spinal root level or “radic” along the path of one or more irritated lumbar nerve roots. In the case of sciatica, this would originate from the L4, L5 and/or Si spinal nerve roots, which make up the sciatic nerve. Radiating pain is also possible from the high lumbar disk herniations in the L3, L2 or L1 regions or from any cervical nerve root in the case of a cervical disk herniation, cervical nerve root irritation or cervical disk degeneration. This pain differs from pain resulting from a facet joint or other spinal structure, which is classified as “referred” pain. Radiating pain is also possible from the high lumbar disc herniations in the L3, L2 or L1 regions or cervical spine regions.

As used herein, “discogenic pain” refers to spinal-related pain that generates from an intervertebral disk. The intervertebral disk suffers from reduced functionality in association with a loss of hydration from the nucleus pulposus. The reduction in functionality coincides with damage in the annulus fibrosus. This weakening can lead to anatomic lesions such as bulging, prolapsed, extruded, or sequestered disc. This weakening can also lead to possible biochemical lesions resulting from leakage of the disk contents that may manifest in back pain or aforementioned chemical radiculopathy.

As used herein, "facet joint pain" or "facetogenic pain" refers to pain generating from the facet joint. "Facet joints" or "zygapophysial joints" are paired, true synovial joints endowed with cartilage, capsule, meniscoid, and synovial membrane.

As used herein the term "low back pain" includes discogenic, facetogenic and radiculopathic pain. The term further includes pain from spinal stenosis. In an embodiment, the spinal stenosis is lumbar spinal stenosis.

As used herein, the term "acute pain" refers to pain lasting up to six months, e.g., five months, four months, three months, two months, four weeks, three weeks, two weeks, one week, six days, five days, four days, three days, two days or one day or less.

As used herein, the term "chronic pain" refers to pain of a duration of longer than six months.

A "patient" or "subject" as used herein means a mammal. In a preferred embodiment, the mammal is a human.

A "positive regulator" as used herein means a cytokine whose level decreases with a decrease in pain.

A "negative regulator" as used herein means a cytokine whose level increases with a decrease in pain.

By way of overview and introduction, systems, methods and processes described relate to the improvement in the selection and administration of treatment options for managing or alleviating pain conditions in patients. For instance, the systems and methods described herein are directed to evaluating and predicting the response of a patient suffering from LBP to an epidural steroid injection. Though the use of the systems and method described herein, a physician is able to predict the efficacy of non-surgical treatments. Using actionable and objective data allows for the selection of the most appropriate treatment for a given patient suffering from a pain condition. Likewise, the systems, methods and processes described herein provide physician and patient with information that can be used to avoid undertaking procedures or treatments that carry the risk of complications where the likelihood of beneficial outcomes are low.

As described in more detail herein, methods, systems and processed are provided for using a predictive model built using linear regression that uses known outcome data to evaluate biometric data associated with a patient. In response to this evaluation, the likelihood that a patient will respond favorably to non-surgical treatment of LBP can be determined. For instance, in one or more configurations, a novel, unique, non-customary evaluative model is used to evaluate the pre-treatment levels of 11 circulating cytokines to predict whether or not a patient will experience significant pain relief following epidural steroid injection (ESI), a common non-surgical treatment for pain relief in HD degeneration and IVD. As shown in the forgoing description, the evaluative model is highly predictive of pain relief following ESI treatment using only 12 independent variables, having an adjusted R2=0.87. Here, 11 of these independent variables are pre-treatment cytokine levels, and one is related to patient demographics (BMI).

Treatment of low back pain was known in the art to be unpredictable. As such, the presently described systems, methods and processes, improve upon the technical field of treatment selection and administration by providing data that permits a physician to select the optimal treatment for a patient with low back pain. The present invention is not only advantageous in providing optimum treatment for certain patients, but it is also a benefit to patients for who are predicted to not benefit from a treatment because the risk of adverse effects and complications from the treatment will be avoided. As such, the described approaches represent a significant improvement in the technical field and are an advancement in the art of treatment administration.

In one or more additional implementations, a blood test performed prior to ESI can be used to obtain the independent variables, and a computer system is configured to evaluate the test results with the predictive model. As a result, a testing kit that combines multiplex assays and computational evaluations is provided that helps physicians and/or patients create individual treatment plans for patients suffering from LBP. Where the independent variables selected are predictive of patient response to other pain treatments, the foregoing approaches can be utilized to determine the likely efficacy of such additional treatments.

In certain embodiments, the present methods and kits provide a predictive panel of cytokine levels in the blood to predict whether or not LBP, e.g., HD degeneration and IVD, patients will experience significant pain relief following ESI. As shown in the figures, tables and descriptions provided herein, patients suffering from low back pain specific to IVD related pathologies (e.g., HD, IVD, spinal stenosis) were found to have unique circulating cytokine profiles compared to control patients. Furthermore, the inventors have determined that the difference in pain intensity (% VAS difference) experienced by a patient with low back pain pre- and post-treatment can be predicted with a model using 12 independent variables (11 pre-treatment blood cytokine levels and body mass index (BMI).

Turning now to FIG. 1, a plot of PCA of serum cytokine profiles measured in control subjects vs. disc disease patients is shown. Such as plot demonstrates independent clusters, indicative of unique circulating cytokine profiles. The top variables in each eigenvector are PC1: T-cell cytokines, PC2: chemokines and DAMPs, PC3: MMPs, PDGFbb. As such, the arrangement of elements, machines, processes and procedures approaches described herein are directed to the identification and evaluation of circulating cytokine profiles that are predictive of pain outcome post treatment can be identified.

Figure 5:
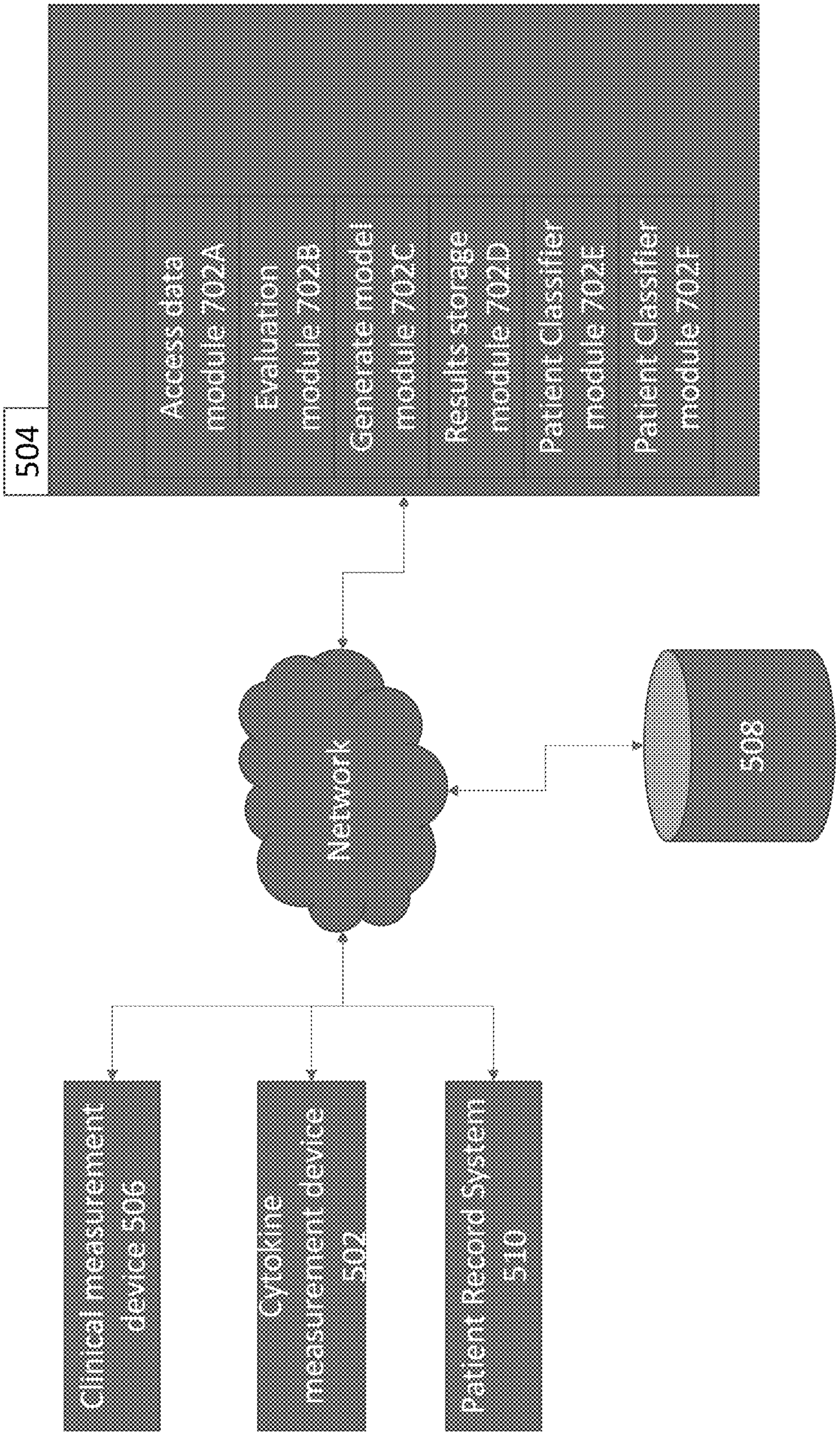
FIG. 5 is a flow diagram of particular steps of the presently described approach.

FIG. 5 presents a block diagram detailing the arrangement of elements, machines, processes and procedures used to evaluate circulating cytokine profiles and other biometric data in order to provide predictions on pain outcome for patients post treatment. As shown in FIG. 5, a biometric measurement device 502 is provided. In one arrangement, the biometric measurement device 502 is one or more measurement assays. In a particular implementation, the biometric measurement device 502 is one or more multiplex assays. In an alternative arrangement, the biometric measurement device 502 can be any device or method known to those possessing an ordinary level of skill in the relevant art used to obtain such measurement data. By way of non-limiting example, the biometric measurement device 502 is a commercial device such as the Bio-Plex® 200 Systems (Biorad), Bio-Plex Pro™ Human Cytokine 27-plex Assay #m500kcaf0y (Biorad), Human MMP 3-Plex Ultra-Sensitive Kit (MSD). In another arrangement, the biometric measurement device 502 is a custom device that is specifically designed and implemented to carry out the measurements of the cytokines described herein.

In a particular configuration, the biometric measurement device 502 evaluates a biological sample from a patient to determine the cytokine levels. For instance, the cytokine measurement device utilizes the patient's blood to determine the patient's cytokine levels. In a further implementation, the blood collected from the sample and evaluated by the cytokine measurement device 502 is collected within about 1 to 2 weeks before an intended treatment date for the patient. As such, the measurement levels obtained by the cytokine measurement device are those levels present for a patient prior to treatment.

In one arrangement, the biometric measurement device 502 is configured to measure the levels of at least 54 cytokines. For instance, the cytokine levels for each of the cytokine shown in Table 1A can be measured by one or more assays comprising the biometric measurement device 502.

TABLE 1A

| Data set: ESI DrawA scaled (each dependent variable was normalized to its mean prior to analysis)<br>Dependent Variables: VAS % Difference<br>Independent variables: Age, BMI, VAS A, ODI A, 53 cytokines: |
|---|
| CRP Draw A |
| HMGB1 Draw A |
| b-NGF Draw A |
| CTACK Draw A |
| Eotaxin Draw A |
| FGF basic Draw A |
| G-CSF Draw A |
| GM-CSF Draw A |
| GROa Draw A |
| HGF Draw A |
| IFN-a2 Draw A |
| IFN-g Draw A |
| IE-10 Draw A |
| IL-12(p70) Draw A |
| IL-12p40 Draw A |
| IL-13 Draw A |
| IL-15 Draw A |
| IL-16 Draw A |
| IL-17 Draw A |
| IL-18 Draw A |
| IL-1a Draw A |
| IL-1b Draw A |
| IL-1ra Draw A |
| IL-2 Draw A |
| IL-2Ra Draw A |
| IL-3 Draw A |
| IL-4 Draw A |
| IL-5 Draw A |
| IL-6 Draw A |
| IL-7 Draw A |
| IL-8 Draw A |
| IL-9 Draw A |
| IP-10 Draw A |
| LIF Draw A |
| MCP-1(MCAF) Draw A |
| MCP-3 Draw A |
| M-CSF Draw A |
| MIF Draw A |
| MIG Draw A |
| MIP-1a Draw A |
| MIP-1b Draw A |
| PDGF-bb Draw A |
| RANTES Draw A |
| SCF Draw A |
| SCGF-b Draw A |
| SDF-1a Draw A |
| TNF-a Draw A |
| TNF-b Draw A |
| TRAIL Draw A |
| VEGF Draw A |
| MMP-1 Draw A |
| MMP-3 Draw A |
| MMP-9 Draw A |

In an alternative arrangement, the biometric measurement device 502 is configured to evaluate a subset of the cytokines provided in Table 1A. For example, the biometric measurement device 502 is configured to measure one or more cytokine levels from the cytokines listed in Table 1B.

TABLE 1B

| Symbol | Alias | Name |
|---|---|---|
| | Negative regulators | |
| IL-1ra | | Interleukin 1 receptor antagonist |
| IL-17 | | Interleukin 17 |
| MIP-1b | CCL4 | C-C Motif Chemokine Ligand 4 |
| GROa | CXCL1 | C-X-C Motif Chemokine Ligand 1 |
| | Positive regulators | |
| MMP-9 | | Matrix Metalloprotease 9 |
| CTACK | CCL27 | C-C Motif Chemokine Ligand 2 |
| LIF | | Leukemia Inhibitory Factor |
| IL-8 | | Interleukin 8 |
| IL-5 | | Interleukin 5 |
| MIP-1a | CCL3 | C-C Motif Chemokine Ligand 3 |
| HGF | | Hepatocyte Growth Factor |

As discussed in more detail herein, in one arrangement, the 11 pre-treatment cytokine levels listed in Table 1B are predictive of patient response to non-surgical treatment of low back pain.

In a further arrangement, a clinical measurement device 506 is used to capture one or more clinical measurements relating to a patient. For example, age, gender, BMI or other demographic data relating to the patient is captured. In one arrangement, the clinical measurement device 506 is a data recording device or computer that is configured to receive user input.

With further reference to FIG. 5, a processor 504 is configured to receive data from both the clinical measurement device 506 and the biometric measurement device 502. In one arrangement, the processor 504 is one or more computing elements (e.g. microprocessor, processor or collections of microprocessors) that are configured to receive and evaluate data according to one or more instruction sets. For example, the processor 504 is configured by a collection of modules (shown as elements 107A-D), configured as code, circuits or software, to implement certain functions and operations with respect to inputs received by one or more data processing devices. For example, a processor 504 is configured by a collection of modules, configured as code or software, to implement certain functions and operations with respect to inputs received (i.e. biometric and clinical data). One or more modules configure the processor 504 to can generate output data that is directly transmitted to a remote computer or other data processing platform.

In one or more implementations, the data generated by the processor 504 is stored or made accessible from a remote storage service, such as but not limited to, a commercial, private or custom cloud-based data hosting service or provider accessible via a network.

In one particular implementation, the processor 504 is configured to receive data from the clinical measurement device 506 and the cytokine measurement device 502 and process such received data using one or more evaluative processes, procedures or algorithms. For example, the processor 504 evaluates the input data using one or more predictive models of circulating cytokine levels in order to predict the response to non-surgical treatments. In another configuration, the processor 504 is configured to generate one or more predictive models to evaluate circulating cytokine levels. In turn, this generated evaluative model can be used classify, categorize or evaluate a particular patient or group of patients. The data that results from evaluating the circulating cytokine using the predictive model is output to local or remote storage such as to database 508 or to the output device such as a patient record system 510.

In a particular embodiment, the database 508 is proprietary database that is accessed remotely using the internet or an intranet and is operable as a remote computing platform (i.e. a cloud platform such as but not limited to Google, IBM, Azure, AWS, etc.) that permits access to and utilization of secure cloud computing services (e.g. data storage, on-demand GPU compute power, applications, etc.).

In a further implementation, the output device, such as a patient record system 510, can in one implementation, include a user terminal or computer that permits data exchanges with the processor 504. For instance, the output device 510 is one or more computers configured to connect to the processor 504 via a network connection. In one or more configurations the output device 510 is configured with software that enables the bidirectional exchange of information with the processor 504. In further implementations, the output device 510 is configured with standard software, such as a web browser, FTP, telnet or other application that permits a user of the output device 510 to send instructions to the processor 504 and receive data in response thereto.

Figure 6:
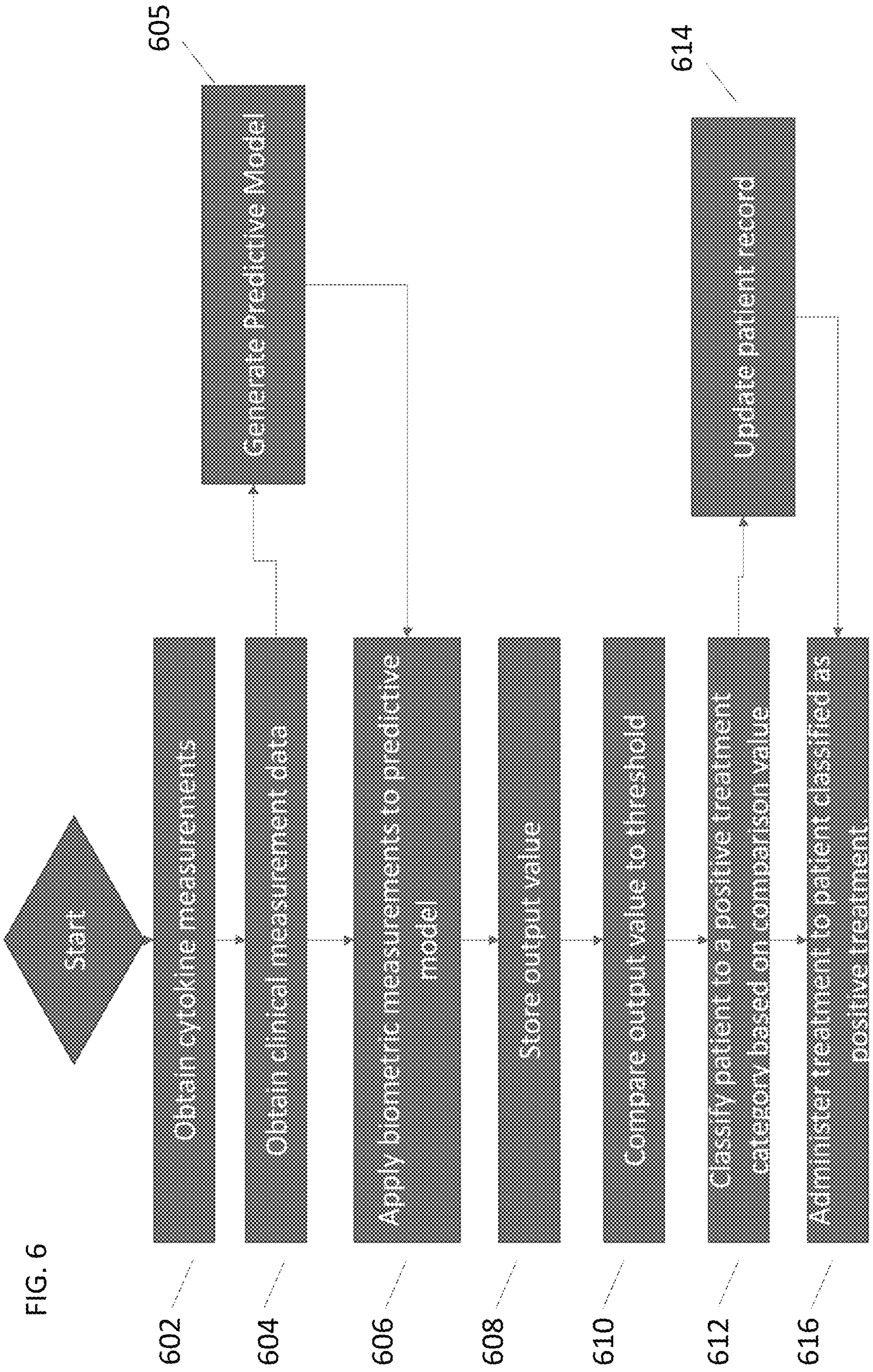
FIG. 6 is a block diagram detailing one or more elements of the presently described approach.

Turning now to the flow diagram of FIG. 6, in one arrangement, upon receipt of an initiation or flag signal, the biometric measurement device 502 is configured to obtain the measurement values of the measured cytokines as in step 602. In one arrangement, an access data module 702A, configured as code executed by the processor 504, configures the processor 504 to access, from the cytokine measurement device 502, the cytokine measurement values. As shown in step 602, one or more assays are used to measure a blood sample of a patient. The measured cytokine values are then output for further processing. In one arrangement, the measurements made by the biometric measurement device 502 are output to a data storage device, such as an electronic record that is associated with the patient. In another arrangement, the measurements made by the biometric measurement device 502 are stored in one or more accessible data storage devices, such as database 508. In another arrangement, the measurements made by the biometric measurement device 502 are transmitted directly to a processor 504 for further evaluation. In one or more configurations, the biometric measurement device 502 includes one or more data transmission devices that are utilized to output data to one or more local or remote data receivers, As shown with respect to step 604, the patient data is generated or accessed by the processor 504. For example, where the clinical measurement device 506 is configured to evaluate the BMI (body mass index) of a patient, such a device is also configured to output such information to the processor 504, a data storage device 508 and/or a patient record system 510. Here, the access data module 702A configures the processor 504 to access the data obtained by the clinical measurement device 506.

In an alternative arrangement, step 604 is carried out by accessing, using a computer or processor configured by the access data module 702A, one or more accessible records for the patient. For example, where a patient record system 510 includes data indicative of the relevant clinical measurement data for the patient, a computer, such as processor 504, is configured to access the patient information from such an electronic record system 510 or database 508.

In yet a further arrangement, both step 602 and 604 can be carried out by accessing patient data stored in one or more databases 508 or other data storage device. Here, both the biometric data and the clinical data are accessible by the computer or processor 504 for further evaluation and analysis.

The data generated according to steps 602 and 604 are communicated to the processor 504 directly through one or more direct physical links, such as serial, RJ45, Parallel, USB, FIREWIRE, eSATA, fiberoptic, or other linkages (as shown in solid lines of FIG. 5). Alternatively, data generated and output to the processor 504 is sent to via one or more wireless or wired communication protocols that utilize a network (such as an intranet or internet) to route data to the intended recipient. In yet a further arrangement, the data acquired in steps 602 and 604 are transmitted wirelessly using one or more RF frequency-based communication protocols, such as Wi-Fi®, Bluetooth®, or Zigbee® protocols to the processor 504 (Wi-Fi® is a registered trademark of the Wi-Fi Alliance. Bluetooth® is a registered trademark of Bluetooth SIG, Inc. Zigbee® is a registered trademark of the Connectivity Standards Alliance). Here, the data sources (e.g. the clinical measurement device 506 and the cytokine measurement device 502) as well as the processor 504 includes one or more network adaptors that allow the data generated to be accessed remotely by processor 504.

With respect to the flow diagram of FIG. 6, in one or more particular implementations, the processor 504 is used to evaluate biometric data using one or more evaluative or predictive models. In another arrangement, the processor 504 is configured to construct or generate one or more evaluating models based on accessible data. In a further implementation, the newly generated model or a prior model are used by the processor 504 to represent or characterize the relative likelihood that a patient will have a positive response to one or more pain treatments.

As shown in step 606, the biometric measurement data (i.e. at least the cytokine measurements and the BMI values) are provided as inputs to an evaluative model configured to generate an output value that corresponds to a pain responsiveness likelihood value.

In one or more arrangements, the processor 504 is configured by an evaluation module 702B to evaluate each biometric value according to the following:

$$VAS=I+(b1*X1)+(b2*X2)+\ldots(bn*Xn)$$

wherein VAS is the pain responsive likelihood value, I is an intercept, and $X_1$-$X_n$ each represent one of the biometric measurement values, and $b_1$-$b_n$ each represent a corresponding coefficient value associated with each of the biometric measurement values. In one or more arrangements, the number of biometric values evaluated by the described model is at least two (2) biometric features, where one of the biometric features is a measurement of a circulating cytokine and one of the biometric features is a measurement value associated with the BMI of the patient. In another configuration, the processor 504 is configured to use 11 cytokine measurements and the measurement value associated with BMI to evaluate a patient. For example, in one arrangement n=12. By way of further example, FIG. 7 presents a table indicating the relevant coefficients for use with particular biometric measurement values. In a further arrangement, one or more of the following cytokines are selected for inclusion as inputs to the evaluative model: Interleukin 1 receptor antagonist (IL-1ra), Interleukin 17 (IL-17), C-C Motif Chemokine Ligand 4 (MIP-1), C-X-C Motif Chemokine Ligand 1 (GROa), Matrix Metalloprotease 9 (MMP-9), C-C Motif Chemokine Ligand 2 (CTACK), Leukemia Inhibitory Factor (LIF), Interleukin 8 (IL-8), Interleukin 5 (IL-5), C-C Motif Chemokine Ligand 3 (MIP-1a), and Hepatocyte Growth Factor (HGF).

In a particular arrangement, the processor 504 is configured by the evaluation module 702B to access an evaluative model, such as in the form of a software package, algorithm, code, or API call, for use in evaluating the patient data. In an alternative configuration, the processor 504 is configured by a model generation module 702C to generate an evaluative model based on prior patient data accessible to the processor 504 as shown in step 605. In one arrangement, the processor 504 is configured to access patient data that includes biometric data.

Figure 2:
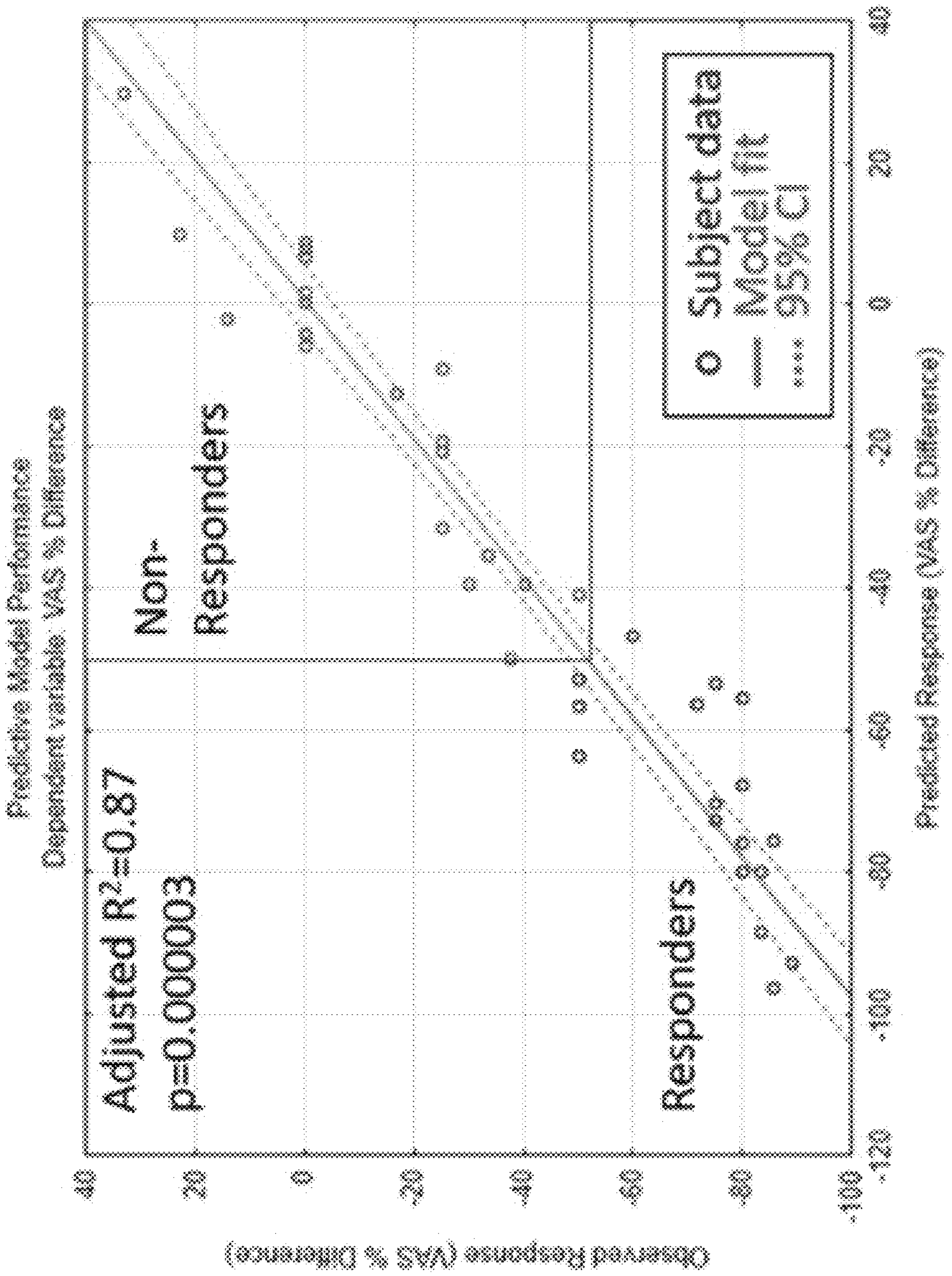
FIG. 2 is a plot that compares experimentally observed response relative to the model predicted.

By way of non-limiting example, the processor 504 is configured to access from the database 508, a dataset of patient data where the patient data includes data on the clinical features of each patient, measurement values for different cytokines and a data value or flag indicating whether the patient has responded favorably to a non-surgical pain treatment. For each patient in the dataset, a data value indicates if the patient responds favorably to epidural steroid injections. Here, the processor 504 is configured to evaluate such data in order to generate a predictive model that can be used on new patients where the treatment response favorability status is unknown. For example, in order to determine treatment favorability based on pre-treatment cytokine levels, the processor 504 is configured to evaluate 54 cytokine levels measured pre-treatment for a number of patients. This dataset is evaluated, in one arrangement, using a stepwise multiple linear regression analysis (STATISTICA). Each of the 54 cytokine levels measured pre-treatment are evaluated numerically for their contribution to the predictive accuracy of the model. Each independent variable found to improve the predictive power of the model is then kept in the model in a stepwise fashion so as to maximize the predictive strength of the model. By way of further example, when such an approach is applied to the cytokines listed in Table 1A, a highly predictive model (adjusted $R2=0.87$) can be generated using 12 independent variables (patient body mass index (BMI) and 11 cytokine levels at pre-treatment). As a regression model of a continuous variable (% VAS difference), this approach predicts patients who are 'non-responders' and 'responders'. FIG. 2 details the predictive performance of the model generated according to step 605 or accessed according to step 606.

In more detail, FIG. 2 and FIG. 7 detail the experimentally observed response (VAS % difference post-treatment vs pre-treatment) relative to the model predicted VAS response (Adjusted $R2=0.87$, $p=0.000003$, $N=55$). Of the 54 cytokines measured, 11 were identified to be significant independent variables for predictive VAS response. Any subject whose VAS % difference was $<-50\%$ (i.e. their pain decrease/improvement was less than 50%) were clinically considered 'non-responders'. Patients whose VAS % difference $>-50\%$ (i.e. their pain decreased more than 50%) were considered 'responders.'

The model generated according to step 605 or accessed according to step 606 is used to generate an output value that correlates to the likelihood that the patient under analysis will be receptive to a particular pain treatment. As shown in step 608, the output value or values generated by the model are derived. In one arrangement, the output values derived are stored by the processor 504 configured with a results storage module 702D. For example, a particular configuration, the processor 504 is configured by one or more software modules to store the output of the model in one or more databases 508 that are accessible remotely from the processor 504.

Turning to step 610, the results of evaluating the patient's biometric data with the evaluative model are compared to a threshold value. For example, in one arrangement the processor 504 is configured by a comparison module that evaluates the derived output value against a threshold value. In one arrangement the threshold value is a pre-determined number. By way of particular implementation, the threshold value is −50. For example, where the output of the predictive model derived according to step 608 is represented as a percentage, the threshold value is also represented as a percentage, such that the threshold value is represented as −50%. By way of example, where predictive model generates a value that is greater than or equal to −50%, the patient is likely to have a favorable response and where the predictive model generates a value that is less than −50%, the patient is likely to have an unfavorable response.

Based on the comparison conducted in step 610, the processor 504 is further configured to classify the patient based on the results of the comparison as shown in step 612. For example, the processor 504 is configured by a classification module 702E, that assigns a data flag, variable or other data object to the patient indicating if they are anticipated to have 'favorable' or 'unfavorable' response to treatment, or otherwise classified as 'responsive' or 'non-responsive.'

In a further arrangement, the processor 504 is configured by an update module 702F to update a record or database entry for the patient to reflect the classified status. For example, where the patient record system 510 is configured to receive data, the processor 504 is configured by the update module 702, as in step 614, to transmit the determined or classified status of the patient. In this way, other health professionals or care providers are presented with the patient's treatment responsiveness prediction at the time of care or consultation. Such a step eliminates the need to conduct multiple different evaluations and provides a single point of reference for the relevant care providers. In an alternative arrangement, the patient classification status is stored to a local or remote memory. For example, a local memory accessible to the processor 504 or database 508 is updated with the additional information. In this configuration, the processor 504 provides a file or data structure navigator that allows a user to locate and access data stored in the respective data storage location.

As shown in step 616, using the information derived from the evaluative model, a patient classified as being receptive to the treatment is treated with the non-surgical pain treatment. For example, a patient whose biometric data is indicative of favorability to treatment, based on evaluation by the predictive model described herein, is treated the with relevant treatment option. For example, based on the evaluation of the patient biometric data, a patient classified as responsive is administered an epidural steroid injection.

In one or more arrangements, the one or more systems or kits can be provided for use in the carrying out the processes described herein. Such system and/or kits may include any or all of the following: assay reagents, buffers, and selective binding partners for the disclosed cytokines, all of which can be housed in a container suitable for transport. In some embodiments, a device to be utilized for the extraction of the biological sample is also included in the kit. In some instances, the kit, thus allows for immediate assessment of the presence and/or level of the cytokine.

In some embodiments, the kit may include materials for administering treatment (e.g., an epidural injection set) and/or one or more therapeutic agents.

In addition, the kits may include instructional materials containing directions (i.e., protocols) for the use of the materials provided in the kit. While the instructional materials typically comprise written or printed materials, they may be provided in any medium capable of storing such instructions and communicating them to an end user. Suitable media include, but are not limited to, electronic storage media (e.g., magnetic discs, tapes, cartridges, chips) and optical media (e.g., CD ROM). The media may include addresses to internet sites that provide the instructional materials.

In a further arrangement, the kit or system provides access to one or more computers that provides the computational functionality provided herein.

EXAMPLES

The present invention may be better understood by reference to the following non-limiting examples, which are presented in order to more fully illustrate embodiments of the invention. They should in no way be construed to limit the scope of the invention.

Example 1

To test if the immune dysfunction is predictive of response to treatment, an investigation was conducted as to whether a change in cytokine profiles may be related to change in pain in patients receiving non-surgical treatment (ESI). Pain intensity (measured with VAS, 1 to 10), and the Oswestry Disability Index (ODI) questionnaire, and blood samples were collected from patients (N=55) before and at first follow up (7-10 days after ESI treatment). Serum samples were assayed for 54 inflammatory mediators using commercial multiplex assays. The results indicated that pain outcome post treatment significantly decreased vs. pre-treatment (9.5±0.9 to 5.5±2.9; p=0.0078), while ODI did not significantly change. A heterogeneity in VAS responses was observed, as expected, with 23 of 55 subjects reporting a positive clinical response (i.e. >50% decrease in VAS). Responders had ≥−50% VAS difference, where the negative sign '−' represents a decrease in VAS difference. Some patients had 0% difference (i.e. no effect of treatment), or positive % VAS difference, indicating that their pain increased slightly post treatment.

Example 2

Subjects were recruited from those receiving ESI treatment for a single level lumbar disc disease (N=55). Prior to treatment, blood samples and patient reported outcomes (PROMs) were evaluated for pain intensity (VAS), and disability (ODI) using questionnaires. Blood samples and PROMs were also collected after treatment at the first follow-up visit. Control subjects with no history of LBP were also recruited (N=57).

Study 1

Cytokine profiles (29 mediators) were measured in samples from patients with disc disease and were compared to levels measured in control subjects. Complete cytokine profiles were compared using principal component analysis (PCA).

As shown in FIG. 1, the PCA of serum cytokine profiles measured in control subjects vs. disc disease patients demonstrated independent clusters are indicative of unique circulating cytokine profiles. Top variables in each eigenvector are PC1: T-cell cytokines, PC2: chemokines and DAMPs, PC3: MMPs, PDGFbb.

Study 2

Serum cytokines were compared in subjects receiving ESI for changes in cytokines pre- and post-treatment. Cytokine changes were analyzed pre- and post-treatment, and compared to VAS change.

Pain outcome post-treatment significantly decreased vs. pre-treatment (9.5±0.9 to 5.5±2.9; p=0.0078), while ODI did not significantly change. A heterogeneity in VAS responses was observed, with 23 of 55 subjects reporting a positive clinical response (i.e., >50% decrease in VAS).

In order to determine if VAS changes (% VAS difference) post treatment can be predicted by pre-treatment cytokine levels, each of the 54 cytokine levels measured pre-treatment were evaluated using a stepwise multiple linear regression analysis (STATISTICA). Each of the 54 cytokine levels measured pre-treatment were evaluated numerically for their contribution to the prediction of % VAS difference post treatment. Each independent variable found to improve the predictive power of the model was kept in the model in a stepwise fashion, to maximize the predictive strength of the model. This approach yielded a highly predictive model (Adjusted R2=0.87) using 12 independent variables (patient body mass index (BMI) and 11 cytokine levels at pre-treatment). As a regression model of a continuous variable (% VAS difference), this approach predicts patients who are 'non-responders' and 'responders'.

The 11 cytokines identified in the model had 2 different types of effects on pain. 7 of 11 cytokines were found to be 'positive regulators' of VAS % difference, suggesting that the levels of the vast majority of cytokines significantly decrease with decrease in pain. However, 4 of 11 cytokines were found to be 'negative regulators' of pain, in that their levels increase with decrease in pain.

As noted, FIG. 2 provides a chart detailing the performance of model for predicting VAS response to ESI treatment based on baseline serum cytokine levels. The chart of FIG. 2 compares the experimentally observed response (VAS % difference post-treatment vs pre-treatment) relative to the model predicted VAS response (Adjusted R2=0.87, p=0.000003, N=55). Of the 54 cytokines measured, 11 were identified to be significant independent variables for predictive VAS response. Any subject whose VAS % difference was <−50% (i.e. their pain decrease/improvement was less than 50%) were clinically considered 'non-responders'. Patients whose VAS % difference >−50% (i.e. their pain decreased more than 50%) were considered 'responders.'

Example 3 Stepwise Regression Analysis

Number of subjects: 57. Using stepwise regression, the variables that best predict % VAS change were analyzed. Thus, the dependent variable was % VAS change and all measured cytokines, age, BMI, ODI A, and VAS A are independent or predictor variables.

A forward stepwise regression analysis was used, which evaluates the independent variables at each step, adding or deleting them from the model based on user-specified criteria provided in Table 1A.

Based on the forward stepwise regression procedure, the subset of factors (independent variables) that best predict % VAS change (dependent variable) contains the variables listed in FIG. 7 (cytokines and BMI).

Here, Table 2 shows a summary of the quality of the regression fit.

TABLE 2

| Statistic | Summary statistics; DV: VAS % Difference (ESI DrawA scaled) Value |
|---|---|
| Multiple R | 0.972270261 |
| Multiple R2 | 0.945309459 |
| Adjusted R2 | 0.872388739 |
| F(20, 15) | 12.9635233 |
| p | 0.00000369224699 |
| Std. Err. of Estimate | 12.916276 |

Likewise, FIG. 7 shows a regression summary for VAS % difference. The regression equation generated from the highlighted cytokines can be generated according to the linear regression derived formula where the b values are the coefficient of each variable, e.g. y-intercept+b1*X1+b2*X2+b3*X3).

As provided previously, the predictive model can be described as:

$$VAS=I+(b1*X1)+(b2*X2)+ \ldots (bn*Xn)$$

wherein VAS is the pain responsive likelihood value, I is an intercept, and X1-Xn each represent one of the biometric measurement values, and b1-bn each represent a corresponding coefficient value associated with each of the biometric measurement values. Using this construction, the values provided in FIG. 7 can be used to determine the % VAS difference. For example:

$$\% \, VAS \text{ difference}=-114.054+21.134*LIF+24.66*\text{CTACK}+56.598*IL17+ \ldots$$

Table 5 shows an analysis of variance, thus confirming the predictive accuracy of the derived predictive model based on cytokine levels and BMI.

TABLE 3

| Effect | Analysis of Variance; DV: VAS % Difference (ESI DrawA scaled) Sums of Squares | df | Mean Squares | F | p-value |
|---|---|---|---|---|---|
| Regress. | 43254.14 | 20 | 2162.707 | 12.96352 | 0.000004 |
| Residual | 2502.45 | 15 | 166.830 | | |
| Total | 45756.59 | | | | |

In order to validate the predictive power of the model derived according to the approach provided herein, Table 4 shows a residual analysis.

TABLE 4

| Raw Residuals | Raw Residual (ESI DrawA scaled.sta) Dependent variable: VAS % Difference | | | | | | | | |
|---|---|---|---|---|---|---|---|---|---|
| Case name −3s . . 0 . . +3s | Observed | Predicted | Residual | Standard | Standard | Std.Err. | Mahalanobis | Deleted | Cook's |
| ESI 103 . . . \| * . . . | −88.8889 | −93.162 | 4.27 | −1.59504 | 0.331 | 6.9619 | 9.20 | 6.023 | 0.003008 |
| ESI 066 . . .* \| . . . | −85.7143 | −75.919 | −9.79 | −1.10456 | −0.758 | 7.8685 | 12.02 | −15.575 | 0.025696 |
| ESI 085 . . . \| *. . . | −85.7143 | −96.510 | 10.80 | −1.69027 | 0.836 | 8.6093 | 14.58 | 19.426 | 0.047856 |
| ESI 042 . . . \| * . . . | −83.3333 | −88.861 | 5.53 | −1.47268 | 0.428 | 9.5159 | 18.03 | 12.089 | 0.022641 |
| ESI 088 . . . *\| . . . | −83.3333 | −80.166 | −3.17 | −1.22536 | −0.245 | 11.4292 | 26.43 | −14.595 | 0.047606 |
| ESI 015 . .* . \| . . . | −80.0000 | −55.853 | −24.15 | −0.53374 | −1.870 | 10.1121 | 20.48 | −62.385 | 0.680886 |
| ESI 029 . . .* \| . . . | −80.0000 | −68.009 | −11.99 | −0.87953 | −0.928 | 8.1636 | 13.01 | −19.968 | 0.045464 |
| ESI 030 . . . *\| . . . | −80.0000 | −76.284 | −3.72 | −1.11494 | −0.288 | 7.7442 | 11.61 | −5.801 | 0.003453 |
| ESI 095 . . . * . . . | −80.0000 | −80.212 | 0.21 | −1.22667 | 0.016 | 8.3720 | 13.73 | 0.366 | 0.000016 |
| ESI 009 * . . \| . . . | −77.7778 | 1829.839 | −1907.62 | 53.10650 | −147.691 | 565.7642 | 67151.87 | 0.995 | 0.541932 |
| ESI 005 . . . * \| . . . | −75.0000 | −70.531 | −4.47 | −0.95127 | −0.346 | 9.5385 | 18.12 | −9.830 | 0.015043 |
| ESI 031 . . . *\| . . . | −75.0000 | −73.052 | −1.95 | −1.02300 | −0.151 | 9.4771 | 17.87 | −4.219 | 0.002735 |
| ESI 052 . .* . \| . . . | −75.0000 | −53.618 | −21.38 | −0.47016 | −1.655 | 10.9603 | 24.23 | −76.384 | 1.199174 |
| ESI 098 . . * \| . . . | −71.4286 | −56.745 | −14.68 | −0.55911 | −1.137 | 9.9108 | 19.63 | −35.707 | 0.214273 |
| ESI 021 . . * \| . . . | −60.0000 | −47.054 | −12.95 | −0.28344 | −1.002 | 9.0090 | 16.06 | −25.212 | 0.088268 |
| ESI 001 . . . \| * . . . | −50.0000 | −57.004 | 7.00 | −0.56648 | 0.542 | 10.3574 | 21.53 | 19.620 | 0.070651 |
| ESI 003 . . . * \| . . . | −50.0000 | −41.037 | −8.96 | −0.11229 | −0.694 | 9.8622 | 19.43 | −21.495 | 0.076885 |
| ESI 045 . . . \| * . . | −50.0000 | −63.963 | 13.96 | −0.76446 | 1.081 | 8.3961 | 13.82 | 24.181 | 0.070524 |
| ESI 051 . . . \|* . . . | −50.0000 | −53.242 | 3.24 | −0.45948 | 0.251 | 11.2319 | 25.49 | 13.298 | 0.038171 |
| ESI 062 . . . \| . . * | −50.0000 | −138.048 | 88.05 | −2.87186 | 6.817 | 17.9613 | 66.71 | −94.295 | 4.907730 |
| ESI 078 . . . * . . . | −40.0000 | −39.714 | −0.29 | −0.07467 | −0.022 | 12.0781 | 29.63 | −2.276 | 0.001293 |
| ESI 057 . . . \| * . . | −37.5000 | −50.182 | 12.68 | −0.37243 | 0.982 | 6.5869 | 8.13 | 17.140 | 0.021807 |
| ESI 026 . . . \|* . . . | −33.3333 | −35.505 | 2.17 | 0.04507 | 0.168 | 8.9761 | 15.93 | 4.200 | 0.002431 |
| ESI 070 . . . \| *. . . | −30.0000 | −39.580 | 9.58 | −0.07085 | 0.742 | 10.6049 | 22.62 | 29.397 | 0.166285 |
| ESI 047 . . . *\| . . . | −25.0000 | −20.902 | −4.10 | 0.46046 | −0.317 | 10.3067 | 21.31 | −11.281 | 0.023130 |
| ESI 067 . . *. \| . . . | −25.0000 | −9.274 | −15.73 | 0.79123 | −1.218 | 10.2138 | 20.91 | −41.970 | 0.314397 |
| ESI 069 . . . *\| . . . | −25.0000 | −19.674 | −5.33 | 0.49539 | −0.412 | 10.4110 | 21.77 | −15.203 | 0.042863 |
| ESI 093 . . . \| *. . . | −25.0000 | −31.743 | 6.74 | 0.15208 | 0.522 | 10.8116 | 23.55 | 22.526 | 0.101478 |
| ESI 071 . . . *\| . . . | −16.6667 | −12.724 | −3.94 | 0.69308 | −0.305 | 11.3850 | 26.22 | −17.674 | 0.069274 |
| ESI 023 . . . \| * . . . | 0.0000 | −4.318 | 4.32 | 0.93220 | 0.334 | 12.3948 | 31.26 | 54.581 | 0.783055 |
| ESI 025 . . . \| * . . . | 0.0000 | −6.222 | 6.22 | 0.87806 | 0.482 | 10.2387 | 21.02 | 16.742 | 0.050273 |
| ESI 044 . . . * \| . . . | 0.0000 | 8.458 | −8.46 | 1.29563 | −0.655 | 8.2951 | 13.46 | −14.395 | 0.024394 |
| ESI 048 . . . * \| . . . | 0.0000 | 7.697 | −7.70 | 1.27398 | −0.596 | 10.8786 | 23.86 | −26.482 | 0.141998 |
| ESI 077 . . . * . . . | 0.0000 | 1.371 | −1.37 | 1.09403 | −0.106 | 8.1898 | 13.10 | −2.292 | 0.000603 |
| ESI 096 . . . * \| . . . | 0.0000 | 6.316 | −6.32 | 1.23470 | −0.489 | 11.3809 | 26.20 | −28.243 | 0.176770 |
| ESI 099 . . . * . . . | 0.0000 | 0.061 | −0.06 | 1.05677 | −0.005 | 12.9139 | 34.02 | −167.080 | 7.965240 |
| ESI 102 . . . \| * . . . | 0.0000 | −4.226 | 4.23 | 0.93482 | 0.327 | 11.1712 | 25.21 | 16.773 | 0.060072 |
| ESI 073 . . . \| .* . . | 14.2857 | −2.321 | 16.61 | 0.98902 | 1.286 | 7.0999 | 9.60 | 23.797 | 0.048842 |
| ESI 065 . . . \| * . . | 23.0769 | 9.587 | 13.49 | 1.32775 | 1.044 | 9.2550 | 17.00 | 27.725 | 0.112645 |
| ESI 079 . . . \| * . . . | 33.3333 | 29.432 | 3.90 | 1.89226 | 0.302 | 11.0490 | 24.64 | 14.545 | 0.044188 |
| Minimum * . . \| . . . | −88.8889 | −138.048 | −1907.62 | −2.87186 | −147.691 | 6.5869 | 8.13 | −167.080 | 0.000016 |
| Maximum . . . \| . . * | 33.3333 | 1829.839 | 88.05 | 53.10650 | 6.817 | 565.7642 | 67151.87 | 54.581 | 7.965240 |

TABLE 4-continued

| Raw Residuals | Raw Residual (ESI DrawA scaled.sta) Dependent variable: VAS % Difference | | | | | | | | |
|---|---|---|---|---|---|---|---|---|---|
| Case name −3s . . 0 . . +3s | Observed | Predicted | Residual | Standard | Standard | Std.Err. | Mahalanobis | Deleted | Cook's |
| Mean * . . \| . . . | −40.4499 | 6.178 | −46.63 | 1.23077 | −3.610 | 23.8872 | 1699.08 | −9.723 | 0.456326 |
| Median . . . * . . . | −45.0000 | −40.376 | −0.83 | −0.09348 | −0.064 | 10.1629 | 20.70 | −3.256 | 0.049558 |

As shown in Table 5, two subjects had a residual that is >2 standard deviations. Thus, they were removed as outliers (ESI 009, ESI 062).

TABLE 5

| Standard Residuals Case name | Standard Residual: VAS % Difference (ESI DrawA scaled) Outliers | | | | | |
|---|---|---|---|---|---|---|
| −5. −4. −3. ±2. 3. 4. 5. | Observed | Predicted | Residual | Standard | Standard | Std.Err. |
| ESI 009 * . . \| . . . | −77.7778 | 1829.839 | −1907.62 | 53.10650 | −147.691 | 565.7642 |
| ESI 062 . . . \| . . * | −50.0000 | −138.048 | 88.05 | −2.87186 | 6.817 | 17.9613 |
| Minimum * . . \| . . . | −77.7778 | −138.048 | −1907.62 | −2.87186 | −147.691 | 17.9613 |
| Maximum . . . \| . . * | −50.0000 | 1829.839 | 88.05 | 53.10650 | 6.817 | 565.7642 |
| Mean * . . \| . . . | −63.8889 | 845.895 | −909.78 | 25.11732 | −70.437 | 291.8628 |
| Median * . . \| . . . | −63.8889 | 845.895 | −909.78 | 25.11732 | −70.437 | 291.8628 |

As shown in the Table 6 evaluation of Mahalanobis distances, 1 subject had a very high level (out of pattern). This subject was removed (ESI 009).

TABLE 6

| Mahalanobis distances | Mahalanobis distances (ESI DrawA scaled.sta) Dependent variable: VAS % Difference | | | | | | | | |
|---|---|---|---|---|---|---|---|---|---|
| Case name 8.13 . . . . . 67E3 | Observed | Predicted | Residual | Standard | Standard | Std.Err. | Mahalanobis | Deleted | Cook's |
| ESI 103 .* . . \| . . . | −88.8889 | −93.162 | 4.27 | −1.59504 | 0.331 | 6.9619 | 9.20 | 6.023 | 0.003008 |
| ESI 066 .* . . \| . . . | −85.7143 | −75.919 | −9.79 | −1.10456 | −0.758 | 7.8685 | 12.02 | −15.575 | 0.025696 |
| ESI 085 .* . . \| . . . | −85.7143 | −96.510 | 10.80 | −1.69027 | 0.836 | 8.6093 | 14.58 | 19.426 | 0.047856 |
| ESI 042 .* . . \| . . . | −83.3333 | −88.861 | 5.53 | −1.47268 | 0.428 | 9.5159 | 18.03 | 12.089 | 0.022641 |
| ESI 088 .* . . \| . . . | −83.3333 | −80.166 | −3.17 | −1.22536 | −0.245 | 11.4292 | 26.43 | −14.595 | 0.047606 |
| ESI 015 .* . . \| . . . | −80.0000 | −55.853 | −24.15 | −0.53374 | −1.870 | 10.1121 | 20.48 | −62.385 | 0.680886 |
| ESI 029 .* . . \| . . . | −80.0000 | −68.009 | −11.99 | −0.87953 | −0.928 | 8.1636 | 13.01 | −19.968 | 0.045464 |
| ESI 030 .* . . \| . . . | −80.0000 | −76.284 | −3.72 | −1.11494 | −0.288 | 7.7442 | 11.61 | −5.801 | 0.003453 |
| ESI 095 .* . . \| . . . | −80.0000 | −80.212 | 0.21 | −1.22667 | 0.016 | 8.3720 | 13.73 | 0.366 | 0.000016 |
| ESI 009 . . . \| . . * | −77.7778 | 1829.839 | −1907.62 | 53.10650 | −147.691 | 565.7642 | 67151.87 | 0.995 | 0.541932 |
| ESI 005 .* . . \| . . . | −75.0000 | −70.531 | −4.47 | −0.95127 | −0.346 | 9.5385 | 18.12 | −9.830 | 0.015043 |
| ESI 031 .* . . \| . . . | −75.0000 | −73.052 | −1.95 | −1.02300 | −0.151 | 9.4771 | 17.87 | −4.219 | 0.002735 |
| ESI 052 .* . . \| . . . | −75.0000 | −53.618 | −21.38 | −0.47016 | −1.655 | 10.9603 | 24.23 | −76.384 | 1.199174 |
| ESI 098 .* . . \| . . . | −71.4286 | −56.745 | −14.68 | −0.55911 | −1.137 | 9.9108 | 19.63 | −35.707 | 0.214273 |
| ESI 021 .* . . \| . . . | −60.0000 | −47.054 | −12.95 | −0.28344 | −1.002 | 9.0090 | 16.06 | −25.212 | 0.088268 |
| ESI 001 .* . . \| . . . | −50.0000 | −57.004 | 7.00 | −0.56648 | 0.542 | 10.3574 | 21.53 | 19.620 | 0.070651 |
| ESI 003 .* . . \| . . . | −50.0000 | −41.037 | −8.96 | −0.11229 | −0.694 | 9.8622 | 19.43 | −21.495 | 0.076885 |
| ESI 045 .* . . \| . . . | −50.0000 | −63.963 | 13.96 | −0.76446 | 1.081 | 8.3961 | 13.82 | 24.181 | 0.070524 |
| ESI 051 .* . . \| . . . | −50.0000 | −53.242 | 3.24 | −0.45948 | 0.251 | 11.2319 | 25.49 | 13.298 | 0.038171 |
| ESI 062 .* . . \| . . . | −50.0000 | −138.048 | 88.05 | −2.87186 | 6.817 | 17.9613 | 66.71 | −94.295 | 4.907730 |
| ESI 078 .* . . \| . . . | −40.0000 | −39.714 | −0.29 | −0.07467 | −0.022 | 12.0781 | 29.63 | −2.276 | 0.001293 |
| ESI 057 .* . . \| . . . | −37.5000 | −50.182 | 12.68 | −0.37243 | 0.982 | 6.5869 | 8.13 | 17.140 | 0.021807 |
| ESI 026 .* . . \| . . . | −33.3333 | −35.505 | 2.17 | 0.04507 | 0.168 | 8.9761 | 15.93 | 4.200 | 0.002431 |
| ESI 070 .* . . \| . . . | −30.0000 | −39.580 | 9.58 | −0.07085 | 0.742 | 10.6049 | 22.62 | 29.397 | 0.166285 |
| ESI 047 .* . . \| . . . | −25.0000 | −20.902 | −4.10 | 0.46046 | −0.317 | 10.3067 | 21.31 | −11.281 | 0.023130 |
| ESI 067 .* . . \| . . . | −25.0000 | −9.274 | −15.73 | 0.79123 | −1.218 | 10.2138 | 20.91 | −41.970 | 0.314397 |
| ESI 069 .* . . \| . . . | −25.0000 | −19.674 | −5.33 | 0.49539 | −0.412 | 10.4110 | 21.77 | −15.203 | 0.042863 |
| ESI 093 .* . . \| . . . | −25.0000 | −31.743 | 6.74 | 0.15208 | 0.522 | 10.8116 | 23.55 | 22.526 | 0.101478 |
| ESI 071 .* . . \| . . . | −16.6667 | −12.724 | −3.94 | 0.69308 | −0.305 | 11.3850 | 26.22 | −17.674 | 0.069274 |
| ESI 023 .* . . \| . . . | 0.0000 | −4.318 | 4.32 | 0.93220 | 0.334 | 12.3948 | 31.26 | 54.581 | 0.783055 |
| ESI 025 .* . . \| . . . | 0.0000 | −6.222 | 6.22 | 0.87806 | 0.482 | 10.2387 | 21.02 | 16.742 | 0.050273 |
| ESI 044 .* . . \| . . . | 0.0000 | 8.458 | −8.46 | 1.29563 | −0.655 | 8.2951 | 13.46 | −14.395 | 0.024394 |
| ESI 048 .* . . \| . . . | 0.0000 | 7.697 | −7.70 | 1.27398 | −0.596 | 10.8786 | 23.86 | −26.482 | 0.141998 |
| ESI 077 .* . . \| . . . | 0.0000 | 1.371 | −1.37 | 1.09403 | −0.106 | 8.1898 | 13.10 | −2.292 | 0.000603 |
| ESI 096 .* . . \| . . . | 0.0000 | 6.316 | −6.32 | 1.23470 | −0.489 | 11.3809 | 26.20 | −28.243 | 0.176770 |
| ESI 099 .* . . \| . . . | 0.0000 | 0.061 | −0.06 | 1.05677 | −0.005 | 12.9139 | 34.02 | −167.080 | 7.965240 |
| ESI 102 .* . . \| . . . | 0.0000 | −4.226 | 4.23 | 0.93482 | 0.327 | 11.1712 | 25.21 | 16.773 | 0.060072 |
| ESI 073 .* . . \| . . . | 14.2857 | −2.321 | 16.61 | 0.98902 | 1.286 | 7.0999 | 9.60 | 23.797 | 0.048842 |

TABLE 6-continued

| Mahalanobis distances | Mahalanobis distances (ESI DrawA scaled.sta) Dependent variable: VAS % Difference | | | | | | | | |
|---|---|---|---|---|---|---|---|---|---|
| Case name 8.13 . . . . . 67E3 | Observed | Predicted | Residual | Standard | Standard | Std.Err. | Mahalanobis | Deleted | Cook's |
| ESI 065 .* . . ǀ . . . | 23.0769 | 9.587 | 13.49 | 1.32775 | 1.044 | 9.2550 | 17.00 | 27.725 | 0.112645 |
| ESI 079 .* . . ǀ . . . | 33.3333 | 29.432 | 3.90 | 1.89226 | 0.302 | 11.0490 | 24.64 | 14.545 | 0.044188 |
| Minimum .* . . ǀ . . . | −88.8889 | −138.048 | −1907.62 | −2.87186 | −147.691 | 6.5869 | 8.13 | −167.080 | 0.000016 |
| Maximum . . . ǀ . . * | 33.3333 | 1829.839 | 88.05 | 53.10650 | 6.817 | 565.7642 | 67151.87 | 54.581 | 7.965240 |
| Mean .* . . ǀ . . . | −40.4499 | 6.178 | −46.63 | 1.23077 | −3.610 | 23.8872 | 1699.08 | −9.723 | 0.456326 |
| Median .* . . ǀ . . . | −45.0000 | −40.376 | −0.83 | −0.09348 | −0.064 | 10.1629 | 20.70 | −3.256 | 0.049558 |

Figure 3:
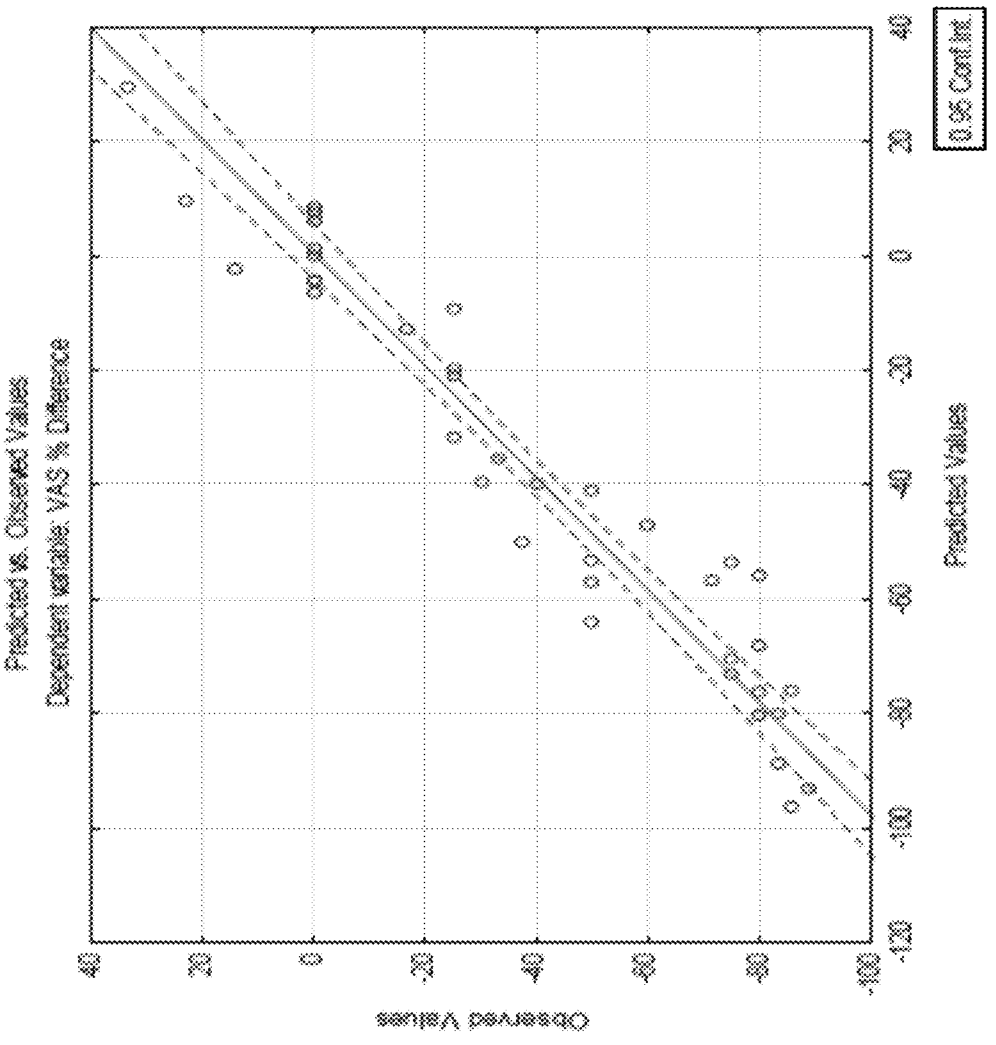
FIG. 3 is a plot that shows the model fit after removal of subjects ESI 009 and ESI 062.
Figure 4:
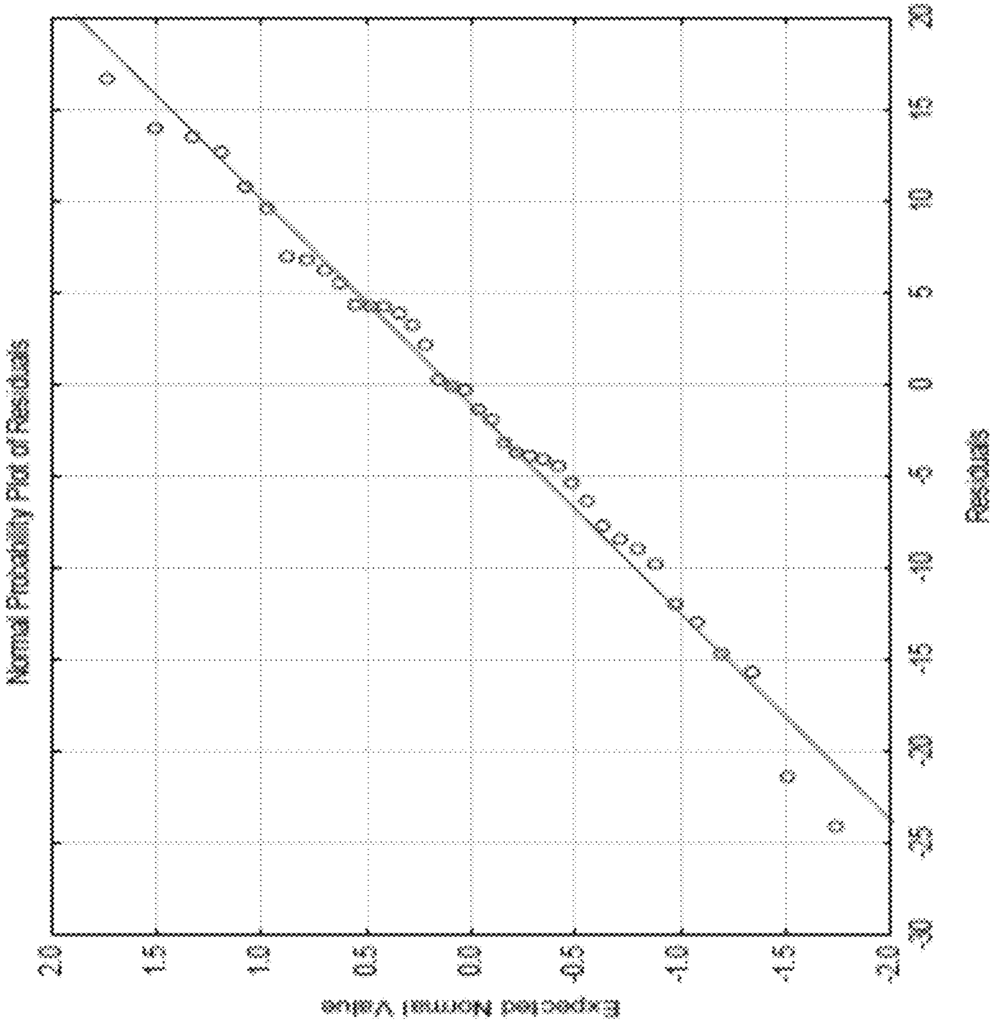
FIG. 4 is a plot that shows a normal probability of residual after removal of the 2 outlier subjects from the data set.

As shown in FIG. 3, the model fit is provided after removal of ESI 009 and ESI 062. FIG. 4 provides a normal probability plot of residual after removal of the 2 outliers from the data set. In further support of the predictive nature of the model derived according to the present disclosure, Table 7 shows a summary of predicted residuals using the regression model.

TABLE 7

| | Predicted & Residual Values VAS % Difference | | | | | | | | |
|---|---|---|---|---|---|---|---|---|---|
| | Observed Value | Predicted Value | Residual | Standard Pred. v. | Standard Residual | Std.Err. Pred. Val | Mahalanobis Distance | Deleted Residual | Cook's Distance |
| ESI 103 | −88.888885 | −93.162132 | 4.273247 | −1.595043 | 0.330842 | 6.961936 | 9.196197 | 6.023122 | 0.003008 |
| ESI 066 | −85.714287 | −75.919327 | −9.794960 | −1.104555 | −0.758342 | 7.868476 | 12.016747 | −15.575082 | 0.025696 |
| ESI 085 | −85.714287 | −96.509735 | 10.795448 | −1.690268 | 0.835802 | 8.609282 | 14.577665 | 19.426144 | 0.047856 |
| ESI 042 | −83.333336 | −88.860550 | 5.527214 | −1.472680 | 0.427926 | 9.515906 | 18.025160 | 12.088802 | 0.022641 |
| ESI 088 | −83.333336 | −80.166168 | −3.167168 | −1.225360 | −0.245207 | 11.429215 | 26.432554 | −14.594813 | 0.047606 |
| ESI 015 | −80.000000 | −55.852806 | −24.147194 | −0.533744 | −1.869517 | 10.112142 | 20.480368 | −62.384747 | 0.680886 |
| ESI 029 | −80.000000 | −68.008759 | −11.991241 | −0.879531 | −0.928382 | 8.163622 | 13.009453 | −19.967978 | 0.045464 |
| ESI 030 | −80.000000 | −76.284355 | −3.715645 | −1.114938 | −0.287672 | 7.744168 | 11.609582 | −5.800983 | 0.003453 |
| ESI 095 | −80.000000 | −80.212051 | 0.212051 | −1.226665 | 0.016417 | 8.371960 | 13.732189 | 0.365685 | 0.000016 |
| ESI 009 | −77.777779 | 1829.838501 | −1907.616333 | 53.106503 | −147.690887 | 565.764221 | 67151.867188 | 0.994766 | 0.541932 |
| ESI 005 | −75.000000 | −70.530800 | −4.469200 | −0.951273 | −0.346013 | 9.538538 | 18.115631 | −9.830352 | 0.015043 |
| ESI 031 | −75.000000 | −73.052277 | −1.947723 | −1.022999 | −0.150796 | 9.477073 | 17.870420 | −4.219150 | 0.002735 |
| ESI 052 | −75.000000 | −53.617714 | −21.382286 | −0.470165 | −1.655453 | 10.960340 | 24.230154 | −76.383827 | 1.199174 |
| ESI 098 | −71.428574 | −56.744534 | −14.684040 | −0.559110 | −1.136863 | 9.910817 | 19.634663 | −35.707447 | 0.214273 |
| ESI 021 | −60.000000 | −47.053627 | −12.946373 | −0.283443 | −1.002330 | 9.009036 | 16.055246 | −25.211979 | 0.088268 |
| ESI 001 | −50.000000 | −57.003681 | 7.003681 | −0.566482 | 0.542237 | 10.357428 | 21.533720 | 19.619635 | 0.070651 |
| ESI 003 | −50.000000 | −41.037010 | −8.962990 | −0.112295 | −0.693930 | 9.862243 | 19.433163 | −21.494547 | 0.076885 |
| ESI 045 | −50.000000 | −63.963364 | 13.963364 | −0.764456 | 1.081067 | 8.396091 | 13.817078 | 24.181139 | 0.070524 |
| ESI 051 | −50.000000 | −53.242268 | 3.242268 | −0.459485 | 0.251022 | 11.231892 | 25.494444 | 13.298363 | 0.038171 |
| ESI 062 | −50.000000 | −138.047729 | 88.047729 | −2.871855 | 6.816804 | 17.961294 | 66.709068 | −94.294640 | 4.907730 |
| ESI 078 | −40.000000 | −39.714165 | −0.285835 | −0.074665 | −0.022130 | 12.078126 | 29.632786 | −2.276280 | 0.001293 |
| ESI 057 | −37.500000 | −50.182014 | 12.682014 | −0.372433 | 0.981863 | 6.586947 | 8.130301 | 17.139526 | 0.021807 |
| ESI 026 | −33.333332 | −35.504852 | 2.171520 | 0.045073 | 0.168123 | 8.976122 | 15.931055 | 4.199833 | 0.002431 |
| ESI 070 | −30.000000 | −39.579880 | 9.579880 | −0.070845 | 0.741691 | 10.604897 | 22.622038 | 29.397110 | 0.166285 |
| ESI 047 | −25.000000 | −20.902027 | −4.097973 | 0.460464 | −0.317272 | 10.306678 | 21.313709 | −11.281129 | 0.023130 |
| ESI 067 | −25.000000 | −9.274297 | −15.725703 | 0.791225 | −1.217511 | 10.213747 | 20.913635 | −41.969929 | 0.314397 |
| ESI 069 | −25.000000 | −19.674236 | −5.325764 | 0.495389 | −0.412330 | 10.410981 | 21.767057 | −15.203163 | 0.042863 |
| ESI 093 | −25.000000 | −31.742933 | 6.742933 | 0.152084 | 0.522049 | 10.811604 | 23.550785 | 22.525801 | 0.101478 |
| ESI 071 | −16.666666 | −12.724433 | −3.942233 | 0.693083 | −0.305214 | 11.385010 | 26.220974 | −17.674091 | 0.069274 |
| ESI 023 | 0.000000 | −4.318364 | 4.318364 | 0.932201 | 0.334335 | 12.394791 | 31.258631 | 54.580978 | 0.783055 |
| ESI 025 | 0.000000 | −6.221732 | 6.221732 | 0.878058 | 0.481697 | 10.238734 | 21.020855 | 16.741901 | 0.050273 |
| ESI 044 | 0.000000 | 8.457607 | −8.457607 | 1.295626 | −0.654802 | 8.295149 | 13.463607 | −14.394758 | 0.024394 |
| ESI 048 | 0.000000 | 7.696588 | −7.696588 | 1.273978 | −0.595883 | 10.878592 | 23.855610 | −26.482119 | 0.141998 |
| ESI 077 | 0.000000 | 1.370758 | −1.370758 | 1.094034 | −0.106126 | 8.189760 | 13.099130 | −2.292385 | 0.000603 |
| ESI 096 | 0.000000 | 6.315691 | −6.315691 | 1.234697 | −0.488972 | 11.380857 | 26.201139 | −28.243185 | 0.176770 |
| ESI 099 | 0.000000 | 0.060818 | −0.060818 | 1.056771 | −0.004709 | 12.913925 | 34.015038 | −167.080383 | 7.965240 |

Thus, the present disclosure provides for the development and use of highly predictive model (R2-0.87) based on circulating cytokine levels as a biomarker signature to predict response to epidural steroid treatment of low back pain.

In one or more further implementations of the system method and approaches described, improved methods and kits for treating patients with low back pain are provided. In a particular configuration, methods for providing non-surgical treatment to patients with low back pain are provided. More particularly, methods for improving epidural steroid treatment of low back pain in a patient are provided.

By way of further and additional background, low back pain (LBP) is the leading cause of disability worldwide, resulting in significant economic burden. Two common causes of LBP are herniated discs (HD) and intervertebral disc degeneration (IVD). Intervertebral disc (IVD) degeneration is a leading cause of disability, resulting in significant economic burden (~$100 billion per year). Treatments for LBP can be non-surgical (e.g., analgesics, muscle relaxants, epidural steroid injections (ESI)) or surgical (e.g., decompressing impinged nerves, removing the inflammatory material (discectomy)). Treatments remain controversial, because patient responsiveness varies widely, and because there are no reliable methods to predict response to treatment.

In one embodiment a predictive model uses certain circulating cytokine levels to predict response to non-surgical treatment of LBP. The instant invention provides methods and kits based on a novel model that uses the pre-treatment levels of 11 circulating cytokines to predict whether or not a patient will experience significant pain relief following epidural steroid injection (ESI), a common non-surgical treatment for pain relief in HD degeneration and IVD. This is a highly predictive model, with an adjusted R2=0.87 and 12 independent variables. 11 of these independent variables are pre-treatment cytokine levels, and one is related to patient demographics (BMI). This technology can be implemented as a blood test performed prior to ESI, which will help physicians create individual treatment plans for LBP patients. The instant invention can further be used to predict patient responses to additional non-surgical treatments.

In certain embodiments, the present methods and kits provide a predictive panel of cytokine levels in the blood to predict whether or not LBP, e.g., HD degeneration and IVD, patients will experience significant pain relief following ESI.

In certain embodiments, a method of selecting treating for a patient with low back pain, which includes the steps of:

measuring the level of Interleukin 1 receptor antagonist (IL-1ra), Interleukin 17 (IL-17), C-C Motif Chemokine Ligand 4 (MIP-1), C-X-C Motif Chemokine Ligand 1 (GROa), Matrix Metalloprotease 9 (MMP-9), C-C Motif Chemokine Ligand 2 (CTACK), Leukemia Inhibitory Factor (LIF), Interleukin 8 (IL-8), Interleukin 5 (IL-5), C-C Motif Chemokine Ligand 3 (MIP-1a), and Hepatocyte Growth Factor (HGF) in a sample from the patient; measuring the patient's body mass index; analyzing the patient's predicted response to non-surgical treatment using the cytokine levels and body mass index in an algorithm; and selecting the patient for non-surgical treatment if the analysis in step c predicts greater than about 50% improvement.

In an embodiment, the non-surgical treatment is epidural steroid treatment. In a further implementation, a method is provided for treating a patient for low back pain including the steps of: measuring the level of Interleukin 1 receptor antagonist (IL-1ra), Interleukin 17 (IL-17), C-C Motif Chemokine Ligand 4 (MIP-1), C-X-C Motif Chemokine Ligand 1 (GROa), Matrix Metalloprotease 9 (MMP-9), C-C Motif Chemokine Ligand 2 (CTACK), Leukemia Inhibitory Factor (LIF), Interleukin 8 (IL-8), Interleukin 5 (IL-5), C-C Motif Chemokine Ligand 3 (MIP-1a), and Hepatocyte Growth Factor (HGF) in a sample from the patient; measuring the patient's body mass index; analyzing the patient's predicted response to non-surgical treatment using the cytokine levels and body mass index in an algorithm; selecting the patient for non-surgical treatment if the analysis in step c predicts greater than about 50% improvement; and treating the patient with non-surgical treatment.

In a further embodiment, the non-surgical treatment is epidural steroid treatment.

In one aspect of one arrangement, the low back pain is acute. In a further aspect, the low back pain is chronic.

In a further configuration, the sample from the patient is a blood sample.

As described previously, FIG. 1 is a plot of PCA of serum cytokine profiles measured in control subjects vs. disc disease patients, which shows independent clusters, indicative of unique circulating cytokine profiles. Top variables in each eigenvector are PC1: T-cell cytokines, PC2: chemokines and DAMPs, PC3: MMPs, PDGFbb.

As described previously, FIG. 2 compares experimentally observed response (VAS % difference post-treatment vs pre-treatment) relative to the model predicted VAS response (Adjusted R2=0.87, p=0.000003, N=55). Of the 54 cytokines measured, 11 were identified to be significant independent variables for predictive VAS response. Any subject whose VAS % difference was <−50% (i.e. their pain decrease/improvement was less than 50%) were clinically considered 'non-responders'. Patients whose VAS % difference >−50% (i.e. their pain decreased more than 50%) were considered 'responders.'

Furthermore, FIG. 3 shows the model fit after removal of subjects ESI 009 and ESI 062 and FIG. 4 is a normal probability plot of residual after removal of the 2 outlier subjects from the data set.

In one described approach, an improvement in patient care for low back pain is provided. For example, a physician is enabled to predict the efficacy of non-surgical treatments and be guided in choosing the most appropriate treatment for an individual and avoid the risk of complications in a patient who would not benefit from the treatment.

According to one implementation described herein, patients suffering from low back pain specific to IVD related pathologies (e.g., HD, IVD, spinal stenosis) were found to have unique circulating cytokine profiles compared to control patients. Further, according to the present invention, the difference in pain intensity (% VAS difference) experienced by a patient with low back pain pre- and post-treatment can be predicted with a model using 12 independent variables (11 pre-treatment blood cytokine levels and body mass index (BMI).

Treatment of low back pain was known in the art to be unpredictable. The present invention permits a physician to select the optimal treatment for a patient with low back pain. The present invention is not only advantageous in providing optimum treatment for certain patients, but it is also a benefit to patients for who are predicted to not benefit from a treatment because the risk of adverse effects and complications from the treatment will be avoided.

In one approach, the methods, systems and processes described herein are particularly directed to the non-surgical treatment of patients with low back pain. The present invention is more particularly directed to treating patients with low back pain with epidural steroid treatment.

The 11 pre-treatment cytokine levels found to be predictive of patient response to non-surgical treatment of low back pain are shown in Table 1B.

TABLE 1B

| Symbol | Alias | Name |
|---|---|---|
| Negative regulators | | |
| IL-1ra | | Interleukin 1 receptor antagonist |
| IL-17 | | Interleukin 17 |
| MIP-1b | CCL4 | C-C Motif Chemokine Ligand 4 |
| GROa | CXCL1 | C-X-C Motif Chemokine Ligand 1 |
| Positive regulators | | |

TABLE 1B-continued

| Symbol | Alias | Name |
|---|---|---|
| MMP-9 | | Matrix Metalloprotease 9 |
| CTACK | CCL27 | C-C Motif Chemokine Ligand 2 |
| LIF | | Leukemia Inhibitory Factor |
| IL-8 | | Interleukin 8 |
| IL-5 | | Interleukin 5 |
| MIP-1a | CCL3 | C-C Motif Chemokine Ligand 3 |
| HGF | | Hepatocyte Growth Factor |

In one embodiment, the blood collection to determine the patient's cytokine levels is made within about 1 to 2 weeks of treatment.

Cytokine levels according to the present invention can be measured by any method known in the art or later developed for obtaining such measurements, including but not limited to Bio-Plex® 200 Systems (Biorad), Bio-Plex Pro™ Human Cytokine 27-plex Assay #m500kcaf0y (Biorad), Human MMP 3-Plex Ultra-Sensitive Kit (MSD).

By way of further particular implementations:

A method of treating a patient with low back pain comprising:

a. measuring the level of Interleukin 1 receptor antagonist, Interleukin 17, C-C Motif Chemokine Ligand 4, C-X-C Motif Chemokine Ligand 1, Matrix Metalloprotease 9, C-C Motif Chemokine Ligand 2, Leukemia Inhibitory Factor, Interleukin 8, Interleukin 5, C-C Motif Chemokine Ligand 3, and Hepatocyte Growth Factor in a sample from the patient;

b. measuring the patient's body mass index;

c. analyzing the patient's predicted response to non-surgical treatment using the cytokine levels and body mass index in an algorithm; and d. selecting the patient for non-surgical treatment if the analysis in step c predicts greater than about 50% improvement.

The method of any previous implementation wherein the non-surgical treatment is an epidural steroid treatment.

The method of any previous implementation wherein the low back pain is acute low back pain.

The method of any previous implementation wherein the low back pain is chronic low back pain.

A method of treating a patient with low back pain comprising:

a. measuring the level of Interleukin 1 receptor antagonist, Interleukin 17, C-C Motif Chemokine Ligand 4, C-X-C Motif Chemokine Ligand 1, Matrix Metalloprotease 9, C-C Motif Chemokine Ligand 2, Leukemia Inhibitory Factor, Interleukin 8, Interleukin 5, C-C Motif Chemokine Ligand 3, and Hepatocyte Growth Factor in a sample from the patient;

b. measuring the patient's body mass index;

c. analyzing the patient's predicted response to non-surgical treatment using the cytokine levels and body mass index in an algorithm;

d. selecting the patient for non-surgical treatment if the analysis in step c predicts greater than about 50% improvement; and e. treating the patient with non-surgical treatment.

The method of any previous implementation wherein the non-surgical treatment is an epidural steroid treatment.

The method of any previous implementation wherein the low back pain is acute w back pain.

The method of any previous implementation wherein the low back pain is chronic low back pain.

In a further description of practical implementations of the systems, methods and computer products described herein, the foregoing approaches are understood and contemplated:

A method for treating a patient suffering from a pain condition comprising: obtaining a plurality of biometric measurement values for the patient, wherein the plurality of biometric measurement values includes at least (i) a plurality of cytokines measurement levels, and (ii) at least one clinical data value; providing, using a computer configured by code executing therein, the plurality of biometric measurement values as inputs to a predictive model, wherein the predictive model is configured to output a pain responsive likelihood value in response to the input values, wherein the predicative model is derived using a stepwise multiple linear regression analysis of a dataset of treatment outcomes; comparing, using the computer, the pain responsive likelihood value to a pre-determined threshold value, and categorizing, using the computer, the patient as treatment positive where the pain responsive likelihood value is equal to or greater than the threshold value.

The method of any of the preceding, further comprising updating, using a computer, one or more values of an electronic medical record of the patient to reflect the categorization status of the patient.

The method of any of the preceding, further comprising: administering, to a treatment positive categorized patient, a pain treatment.

The method of any of the preceding, wherein the pain treatment is an epidural steroid injection.

The method of any of the preceding, wherein the plurality of cytokines measurement levels are obtained prior to an intended treatment date.

The method of any of the preceding, wherein the plurality of cytokines measurement levels are obtained 1 to 2 weeks of prior to the intended treatment date.

The method of any of the preceding, wherein the predicative model is provided according to:

$$VAS=I+(b1*X1)+(b2*X2)+\ldots(bn*Xn)$$

wherein VAS is the pain responsive likelihood value, I is an intercept, and X1-Xn each represent one of the biometric measurement values, and b1-bn each represent a corresponding coefficient value associated with each of the biometric measurement values.

The method of any of the preceding, wherein n=12.

The method of any of the preceding, wherein the pre-determined threshold value is −50%.

The method of any of the preceding, wherein the cytokine measurements includes measurements of the levels of one or more of: Matrix Metalloprotease; C-C Motif Chemokine Ligand 2; Leukemia Inhibitory Factor; Interleukin 8; Interleukin 5; C-C Motif Chemokine Ligand 3 and Hepatocyte Growth Factor.

The method of any of the preceding, wherein the cytokine measurement values further includes measurements of one or more the following: Interleukin 1 receptor antagonist; Interleukin 17; C-C Motif Chemokine Ligand 4; C-X-C Motif Chemokine Ligand 1 of the patient.

The method of any of the preceding, wherein the clinical data value is a body mass index value.

The method of any of the preceding wherein the pain condition is acute low back pain.

The method of any of the preceding wherein the pain condition is chronic low back pain.

The method of any of the preceding, further comprising: measuring, from a sample, the level of: Interleukin 1 receptor antagonist, Interleukin 17, C-C Motif Chemokine Ligand 4, C-X-C Motif Chemokine Ligand 1, Matrix Metalloprotease 9, C-C Motif Chemokine Ligand 2, Leukemia Inhibitory Factor, Interleukin 8, Interleukin 5, C-C Motif Chemokine Ligand 3, and Hepatocyte Growth Factor present for a patient.

The method of any of the preceding, wherein the sample is a blood sample.

A system for treating a patient suffering from a pain condition comprising: one or more multiplex assays configured to determine circulating cytokine levels of one or more of Interleukin 1 receptor antagonist, Interleukin 17, C-C Motif Chemokine Ligand 4, C-X-C Motif Chemokine Ligand 1, Matrix Metalloprotease 9, C-C Motif Chemokine Ligand 2, Leukemia Inhibitory Factor, Interleukin 8, Interleukin 5, C-C Motif Chemokine Ligand 3, and Hepatocyte Growth Factor for the patient; and a processor, configured by code executing therein, to: receive the circulating cytokine levels measured by the multiplex assays; obtain at least one body mass index value for the patient, a coefficient value for the body mass index value, and at least one coefficient value for each of the circulating cytokine levels provide the body mass index value, the coefficient value for the body mass index value, the circulating cytokine levels and the at least one coefficient value for each of the circulating cytokine levels as inputs to a predictive model, wherein the predictive model is configured to output a pain responsive likelihood value in response to the input values, and the predicative model is derived using a stepwise multiple linear regression analysis of a dataset of treatment outcomes; compare the pain responsive likelihood value to a pre-determined threshold value, categorize the patient as treatment positive where the pain responsive likelihood value is equal to or greater than the threshold value.

The inventor's article, "Profiling Serum cytokines in patients with disc disease: Immune dysregulation and Disease Biomarkers", [European Cells and Materials Vol. NN. Suppl. N, 20xxx, is herein incorporated by reference as if presented in its entirety. [PROPER CITE]. Additionally, all patents, published patent applications, and other publications cited herein are hereby incorporated by reference in their entirety.

As used herein, processors, computing elements and microprocessors described herein are, in one or more implementations, connected, directly or indirectly, to one or more memory storage devices (memories). The memory is a persistent or non-persistent storage device that is operative to store an operating system for the processor in addition to one or more of software modules. In accordance with one or more embodiments, the memory comprises one or more volatile and/or non-volatile memories, such as Read Only Memory ("ROM"), Random Access Memory ("RAM"), Electrically Erasable Programmable Read-Only Memory ("EEPROM"), Phase Change Memory ("PCM"), Single In-line Memory ("SIMM"), Dual In-line Memory ("DIMM") or other memory types. Such memories can be fixed or removable, as is known to those of ordinary skill in the art, such as through the use of removable media cards or modules. The computer memories may also comprise secondary computer memory, such as magnetic or optical disk drives or flash memory, that provide long term storage of data in a manner similar to the persistent memory device. In one or more embodiments, the memories of the processors provide for storage of application programs and data files when needed.

It will be further appreciated that computers, processors or computing devices described herein can communicate with the one or more remote networks using USB, digital input/output pins, eSATA, parallel ports, serial ports, Fire Wire®, Wi-Fi®, Bluetooth®, or other communication interfaces (FireWire® is a registered trademark of Apple Inc). In a particular configuration, computing devices, processors or computers provided herein may be further configurable through hardware and software modules so as to connect to one or more remote servers, computers, peripherals or other hardware using standard or custom communication protocols and settings (e.g., TCP/IP, etc.) either through a local or remote network or through the Internet. Computing devices, processors or computers provided herein may utilizes wired or wireless communication means, such as, but not limited to CDMA, GSM, Ethernet, Wi-Fi®, Bluetooth®, USB, serial communication protocols and hardware to connect to one or more access points, exchanges, network nodes or network routers.

The processors or computers described are configured to execute code written in a standard, custom, proprietary or modified programming language such as a standard set, subset, superset or extended set of JavaScript, PHP, Ruby, R, Scala, Erlang, C, C++, Objective C, Swift, C#, Java, Assembly, Go, Python, Perl, R, Visual Basic, Lisp, or Julia or any other object oriented, functional or other paradigm based programming language.

While this specification contains many specific embodiment details, these should not be construed as limitations on the scope of any embodiment or of what can be claimed, but rather as descriptions of features that can be specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing can be advantageous. Moreover, the separation of various system components in the embodiments described above should not be understood as requiring such separation in all embodiments, and it should be understood that the described program components and systems can generally be integrated together in a single software product or packaged into multiple software products.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

It should be noted that use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having the same name (but for use of the ordinal term) to distinguish the claim elements. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Particular embodiments of the subject matter described in this specification have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain embodiments, multitasking and parallel processing can be advantageous.

Publications and references to various known systems maybe cited throughout this application, the disclosures of which are incorporated herein by reference. Citation of any publications or documents is not intended as an admission that any of them is pertinent prior art, nor does it constitute any admission as to the contents or date of these publications or documents. All references cited herein are incorporated by reference to the same extent as if each individual publication and references were specifically and individually indicated to be incorporated by reference.

While the invention has been particularly shown and described with reference to a preferred embodiment thereof, it will be understood by those skilled in the art that various changes in form and details Although the foregoing invention has been described in detail for purposes of clarity of understanding, it will be apparent that certain changes and modifications can be practiced within the scope of the appended claims. Accordingly, the present embodiments are to be considered as illustrative and not restrictive, and the invention is not to be limited to the details given herein but may be modified within the scope and equivalents of the appended claims.

What is claimed is:

1. A method for treating a patient suffering from a pain condition, comprising:

measuring, from a sample, the levels of Interleukin 1 receptor antagonist (IL-1ra), Interleukin 17 (IL-17), C-C Motif Chemokine Ligand 4 (MIP-1b), C-X-C Motif Chemokine Ligand 1 (GROa), Matrix Metalloprotease 9 (MMP-9), C-C Motif Chemokine Ligand 2 (CTACK), Leukemia Inhibitory Factor (LIF), Interleukin 8 (IL-8), Interleukin 5 (IL-5), C-C Motif Chemokine Ligand 3 (MIP-1a), and Hepatocyte Growth Factor (HGF) present for the patient to obtain a plurality of cytokines measurement levels;

obtaining a plurality of biometric measurement values from the patient, wherein the plurality of biometric measurement values comprises (i) the plurality of cytokines measurement levels, and (ii) at least one clinical data value;

providing, using a computer configured by code executing therein, the plurality of biometric measurement values as inputs to a predictive model, wherein the predictive model is configured to output a pain responsive likelihood value in response to the inputs, wherein the predicative model is derived using a stepwise multiple linear regression analysis of a dataset of treatment outcomes;

comparing, using the computer, the pain responsive likelihood value to a pre-determined threshold value, and categorizing, using the computer, the patient as treatment positive where the pain responsive likelihood value is equal to or greater than the threshold value, and administering a non-surgical pain treatment to a treatment-positive categorized patient, wherein the pain condition is acute low back pain or is chronic low back pain.

2. The method of claim 1, further comprising:

updating, using a computer, one or more values of an electronic medical record of the patient to reflect the categorization status of the patient.

3. The method of claim 1, wherein the non-surgical pain treatment is an epidural steroid injection.

4. The method of claim 1, wherein the plurality of cytokines measurement levels is obtained prior to an intended treatment date.

5. The method of claim 4, wherein the plurality of cytokines measurement levels is obtained 1 to 2 weeks prior to the intended treatment date.

6. The method of claim 1, wherein the predicative model is provided according to:

$$VAS=I+(b_1*X_1)+(b_2*X_2)+ \ldots (b_n*X_n)$$

wherein VAS is the pain responsive likelihood value, I is an intercept, and $X_1$-$X_n$ each represent one of the biometric measurement values, and $b_1$-$b_n$ each represent a corresponding coefficient value associated with each of the biometric measurement values.

7. The method of claim 6, wherein n=12.

8. The method of claim 1, wherein the pre-determined threshold value is −50%.

9. The method of claim 1, wherein the at least one clinical data value is a body mass index value.

10. The method of claim 1, wherein the sample is a blood sample.

* * * * *